United States Patent
Baiocchi et al.

(10) Patent No.: US 9,676,749 B2
(45) Date of Patent: Jun. 13, 2017

(54) COMPOSITIONS AND METHODS FOR CANCER DETECTION AND TREATMENT

(71) Applicant: Ohio State Innovation Foundation, Columbus, OH (US)

(72) Inventors: Robert Baiocchi, Dublin, OH (US); Chenglong Li, Dublin, OH (US); Pui Kai Li, Galloway, OH (US); Fengting Yan, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 14/703,650

(22) Filed: May 4, 2015

(65) Prior Publication Data

US 2016/0052910 A1 Feb. 25, 2016

Related U.S. Application Data

(63) Continuation of application No. 13/518,828, filed as application No. PCT/US2010/061945 on Dec. 22, 2010, now Pat. No. 9,044,432.

(60) Provisional application No. 61/289,301, filed on Dec. 22, 2009, provisional application No. 61/293,890, filed on Jan. 11, 2010.

(51) Int. Cl.
| | |
|---|---|
| *C07D 401/12* | (2006.01) |
| *A61K 31/16* | (2006.01) |
| *C07D 405/12* | (2006.01) |
| *A61K 31/185* | (2006.01) |
| *A61K 31/4439* | (2006.01) |
| *A61K 31/706* | (2006.01) |
| *A61K 45/06* | (2006.01) |

(52) U.S. Cl.
CPC .......... *C07D 401/12* (2013.01); *A61K 31/16* (2013.01); *A61K 31/185* (2013.01); *A61K 31/4439* (2013.01); *A61K 31/706* (2013.01); *A61K 45/06* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 5,116,995 | A | 5/1992 | Nakazato et al. |
| 6,399,631 | B1 | 6/2002 | Elliott et al. |
| 8,080,573 | B2 | 12/2011 | Jones et al. |
| 8,338,437 | B2 | 12/2012 | Wahhab et al. |

FOREIGN PATENT DOCUMENTS

WO WO-2011/079236 6/2011

OTHER PUBLICATIONS

Registry No. 1158483-32-9 (Entered STN Jun. 16, 2009).*
Registry No. 892581-76-9 (Entered STN Jul. 14, 2006).*
Carter, S.K. et al. (Chemotherapy of Cancer; Second edition; John Wiley & Sons: New York, 1981: appendix C).
Final Office Action mailed Aug. 8, 2014 for U.S. Appl. No. 13/518,828.
Gura (Science, 1997, 278:1041-1042).
International Preliminary Report on Patentability issued Jun. 26, 2012 by the International Searching Authority for Application PCT/US2010/061945 filed Dec. 22, 2011 and later published as W0/2011/079236 on Jun. 30, 2011 (Applicant—The Ohio State University Reseach Foundation II Inventor—Robert Baiocchi, et al.) (5 pages).
International Search Report issued Feb. 24, 2011 by the International Searching Authority for Application PCT/US2010/061945 filed Dec. 22, 2011 and later published as W0/2011/079236 on Jun. 30, 2011 (Applicant—The Ohio State University Reseach Foundation Inventor—Robert Baiocchi, et al.) (1 page).
Kaiser (Science, 2006, 313: 1370).
Krontiris and Capizzi (Internal Medicine, 4th edition, Editor-in-Chief Jay Stein, Elsevier Science, 1994 Chapters 71-72, pp. 699-729).
Non-Final Office Action mailed Oct. 30, 2013 for U.S. Appl. No. 13/518,828.
Notice of Allowance mailed Jan. 2, 2015 for U.S. Appl. No. 13/518,828.
Registry Data for 880813-30-9, Entered STN Apr. 18, 2006.
Sali and Blundell, Comparative protein modelling by satisfaction of spatial restraints. J Mal. Biol., 1993. 234(3): 779-815.
Van Noort and Amor (International Rev. of Cytology, 1998, vol. 178, Cell Biology of Autoimmune Diseases, pp. 127-206).
Written Opinion issued Feb. 24, 2011 by the International Searching Authority for Application PCT/US2010/061945 filed Dec. 22, 2011 and later published as W0/2011/079236 on Jun. 30, 2011 (Applicant—The Ohio State University Reseach Foundation // Inventor—Robert Baiocchi, et al.) ( 4 pages).
Zhao, et al., PRMT5-mediated methylation of histone H4R3 recruits DNMT3A, coupling histone and DNA methylation in gene silencing. Nat. Struct. Mal. Biol., 2009. 16(3): 304-311.

* cited by examiner

*Primary Examiner* — James D Anderson
(74) *Attorney, Agent, or Firm* — Baker & Hostetler LLP

(57) ABSTRACT

Disclosed herein are compositions and methods for cancer detection and treatment. Compounds that inhibit PRMT5 are contemplated, as are pharmaceutical compositions comprising a therapeutically effective amount of at least one PRMT5 inhibitor. In some embodiments pharmaceutical compositions further comprising at least one HDAC inhibitor are contemplated. Methods of treating disorders in a mammal by inhibiting PRMT5 by administering to a mammal, a therapeutically effective amount of a PRMT5 inhibitor are also disclosed.

7 Claims, 23 Drawing Sheets

A

B

| MolID | ChemBridge ID | XP GScore (kcal/mol) |
|---|---|---|
| 1 | 9007506 | -9.14 |
| 2 | 7928258 | -9.14 |
| 3 | 9041341 | -8.97 |
| 4 | 9000608 | -8.90 |
| 5 | 9033823 | -8.10 |
| 6 | 5613522 | -7.99 |
| 7 | 9006430 | -7.94 |
| 8 | 9016713 | -7.31 |

Figure 7

COMPOSITIONS AND METHODS FOR CANCER DETECTION AND TREATMENT

CROSS-REFERENCES TO RELATED APPLICATIONS

This applications is a continuation of U.S. application Ser. No. 13/518,828, filed Oct. 26, 2012 and issued as U.S. Pat. No. 9,044,432 on Jun. 2, 2015, which is a National Phase Application of International Application No. PCT/US2010/061945, filed Dec. 22, 2010, which claims priority to U.S. Provisional Patent Application No. 61/289,301, filed Dec. 22, 2009, and U.S. Provisional Patent Application No. 61/293,890, filed Jan. 11, 2010, which applications are incorporated by reference herein in their entirety.

BACKGROUND

High grade astrocytomas are the most common primary central nervous system (CNS) malignancy afflicting nearly 10,000 pediatric and adult patients each year in North America alone. While surgery remains the most effective curative therapy for CNS tumors, grade III (anaplastic astrocytoma) and grade IV (glioblastoma, GBM) astrocytomas exhibit a highly invasive histology that precludes effective surgical resection. Consequently, GBM tumors are among the most malignant cancers with a mean survival of approximately one year despite multimodal therapy with surgery, radiation and chemotherapy. In contrast to many cancers, the survival outcome of patients diagnosed with GBM has improved only marginally over the past several decades. While our understanding of the pathophysiology of these high grade malignancies has improved over the past several years, discovery of effective therapies have been limited as few novel targets affecting the complex pathways dysregulated in GBM have been identified.

Malignant astrocytomas display an impressive spectrum of genetic and epigenetic abnormalities affecting multiple pathways relevant to cell growth, survival and remodeling of the tumor microenvironment. Over the past several years, numerous genome-wide studies have demonstrated that GBM possesses a remarkable degree of heterogeneity with regard to genetic mutation, gene expression profiles, and epigenetic modifications. This degree of biologic heterogeneity has undoubtedly contributed to the challenge of identifying key proteins that are critical to the underlying pathogenesis of this aggressive disease.

Posttranslational modification of proteins is a common activity involved at virtually all levels of cellular regulation. The enzymes that covalently modify amino acids add an additional layer of regulatory control over multiple cellular processes including chromatin remodeling, gene transcription, signal transduction, DNA repair and RNA processing. The enzymes of the protein arginine methyltransferase (PRMT) family represents a group of proteins that are evolutionarily conserved amongst a wide variety of organisms. PRMT enzymes covalently modify both histone and a growing number of proteins that are critical to the maintenance of numerous cellular regulatory networks. The PRMT5 enzyme is a type II arginine methyltransferase that utilizes the donor molecule S-adenosyl-L-methionine to catalyze the transfer of a methyl group to two of three guanidino nitrogen atoms within the arginine molecule. PRMT5 drives the formation of both ω-monomethylarginine and symmetric dimethylarginine residues to affect a wide range of key biologic functions at the level of chromatin to control transcriptional repression and as an enzyme that modulates non-histone protein function.

In addition to classic gene mutations, epigenetic silencing of tumor suppressor genes (TSG) frequently leads to dysregulation of signaling pathways and promotion of tumorigenesis. Chromatin remodeling enzymes like histone deacetylase (HDAC), DNA methyltransferase, and protein arginine methyltransferase 5 (PRMT5) are involved in silencing TSG expression and over expression of these enzymes can promote cellular transformation. Drugs that inhibit HDAC enzymes (HDAC-I) or prevent DNA methylation are currently being examined in clinical trials treating patients with cancer. HDAC-I and hypomethylating agents had been shown to possess anti-tumor activity in malignant gliomas both in vitro and in vivo, however, clinical trials investigating these agents have been disappointing, pointing to the need to identify other promising epigenetic targets. PRMT5 has been shown to methylate histone proteins at H3 arginine 8 (H3R8) and H4R3, and trigger TSG silencing. PRMT5 has either a positive or negative effect on its substrates by arginine methylation when interacting with a number of complexes and is involved in a variety of cellular processes, including RNA processing, signal transduction, transcriptional regulation, and germ cell development. Recent studies showed PRMT5 to be a major pro-survival factor regulating eIF4E expression and p53 translation. PRMT5 depletion triggers p53-dependent apoptosis and sensitized various cancer cells to Tumor necrosis factor (TNF)-related apoptosis-inducing ligand (TRAIL) without affecting TRAIL resistance in non-transformed cells.

Several groups have recently described how PRMT5 dysregulation can affect cell growth. Work previously reported demonstrates that overexpression of PRMT5 is involved in the pathogenesis of mantle cell lymphoma, an aggressive hematologic malignancy. While that work contributed information regarding the mechanism of PRMT5 overexpression, the functional consequences of PRMT5 inhibition on growth and survival of the transformed cell remain poorly characterized. We have found that the PRMT5 enzyme is overexpressed in cell tines derived from high grade astrocytomas and in primary anaplastic astrocytoma and GBM tumors. The degree of PRMT5 overexpression was related to proliferative index of both cell lines and primary tumors and was found to be an independent prognostic factor that could identify patients with more aggressive disease and poor overall survival. Because this enzyme is intimately involved with numerous processes that are frequently dysregulated in cancer, we were led to evaluate the consequences of PRMT5 inhibition in high grade astrocytomas as these cancers display overexpression of PRMT5 in the context of profound molecular heterogeneity. We found that inhibition of PRMT5 overexpression in GBM cells led to restoration of critical regulatory pathways affecting cell growth, survival, and tumor suppressor and immune modulatory gene expression. These findings suggested that experimental therapeutic strategies aimed at inhibiting the effects of PRMT5 overexpression in cancer might lead to a better understanding how to directly and indirectly affect GBM tumor progression.

Identification of novel therapeutic strategies to improve the outcome of patients with high grade astrocytomas has, for the most part, proved elusive to date. This is due to several problems inherent to high grade gliomas including: (1) the degree of molecular heterogeneity; (2) lack of a universal target selectively expressed in the tumor; (3) invasive nature of the disease; (4) rapid evolution of chemo and radiation resistance; and (5) likelihood that high grade gliomas arise as a consequence of cancer stem cell and clonal evolution. Identification of a central factor driving these multiple pathways contributing to growth, survival, invasiveness and resistance has proven difficult.

PRMT5 overexpression in high grade gliomas can serve as an attractive therapeutic target for several reasons. First, PRMT5 is selectively overexpressed in high grade gliomas and not in normal human astrocytes or neighboring primary brain tissue. Second, PRMT5 knock down results in cell cycle arrest, apoptosis, reduced invasiveness and restoration of tumor suppressor and immune modulatory cytokine gene expression. Third, PRMT5 is over expressed in glioma brain tumor stem cells. PRMT5 overexpression is highly relevant to high grade glioma biology and therefore fulfills the criteria of an optimal target for this and other diseases.

DESCRIPTION

High grade astrocytomas are aggressive brain to ors that are associated with a dismal prognosis and are considered incurable with a mean survival of less than one year despite intensive multimodality therapy. The limits of current treatment modalities indicate a need for innovative therapies targeting grade III and grade IV (glioblastoma multiforme, GBM). Recent studies have shown that post translational covalent modification of proteins and epigenetic regulation of chromatin plays a central role in the control of cell growth, differentiation, and proliferation. Chromatin remodeling enzymes like histone deacetylase (HDAC), DNA methyltransferase and protein arginine methyltransferase 5 (PRMT5) are involved in silencing pro inflammatory and tumor suppressor gene (TSG) expression and contribute towards cellular transformation. The PRMT5 enzyme contributes towards transcriptional silencing of several important regulatory genes by methylating arginine residues on histone proteins (at histone 4 arginine residue 3 (H4R3) and (H3R8)).

It is disclosed herein that epigenetic processes driven by PRMT5 over expression are relevant in regulation of key oncogenic pathways that are operable in high grade astrocytomas. Patient-derived GBM cell lines and primary GBM tumors over express abundant levels of PRMT5 protein. Normal brain tissue and low or intermediate grade astrocytomas do not over express PRMT5 suggesting that overexpression may selectively occur in high grade, more aggressive gliomas. The degree of PRMT5 over expression inversely correlated with survival of GBM patients and with proliferation of GBM cell lines.

Small inhibitory RNA molecules (siRNA) are disclosed herein to inhibit PRMT5 expression leading to demethylation of target histone protein arginine residues and transcriptional de-repression and translation of tumor suppressor and immune modulatory gene products Inhibition of PRMT5 overexpression led GBM cells to undergo cell cycle arrest, apoptosis, and complete inhibition of cell migration. PRMT5 knockdown led GBM cell lines to become sensitized to the toxic effects of temazolomide, a drug considered standard of care in upfront therapeutic strategies to treat patients with GBM. It is believed that shown herein is that PRMT5 is both an important prognostic factor and an attractive therapeutic target for GBM. Computational modeling systems utilizing crystallographic structure of homologous PRMT enzymes allowing for construction of a molecular model of PRMT5 and rapid screening of over 10,000 small molecule compounds have been developed. This method has led to the discovery of small molecules that inhibit PRMT5 activity. These novel strategies can be used to generate more potent and selective small molecule inhibitors of PRMT5 activity. Promising compounds can be rigorously evaluated on both in vitro and in vivo development platforms and will enhance the ability to discover a new class of drugs that selectively inhibit a promising therapeutic target in GBM.

It is believed that PRMT5 overexpression is an oncogenic process associated with more aggressive clinical behavior and poor overall survival of patients with high grade astrocytomas. Using siRNA molecules to block PRMT5 expression supports the experimental therapeutic approach to inhibit PRMT5 in GBM.

Additional features and advantages will be set forth in part in the description that follows, and in part will be obvious from the description, or may be learned by practice of the inventions. The objects and advantages of the inventions will be realized and attained by means of the elements and combinations particularly pointed out in the appended claims.

It is to be understood that both the foregoing general description and the following detailed description are exemplary and explanatory only and are not restrictive of the inventions, as claimed.

BRIEF DESCRIPTION OF THE DRAWINGS

The accompanying drawings, which are incorporated in and constitute a part of this specification, illustrate some embodiments of the inventions, and together with the description, serve to explain principles of the inventions.

FIG. 7 shows (A) Virtual screen hits selected for validation in bio-assays. (B) Eight compounds selected for lowest binding energy from a high throughput library screen of 10,000 small molecules.

DETAILED DESCRIPTION

Figure 1:
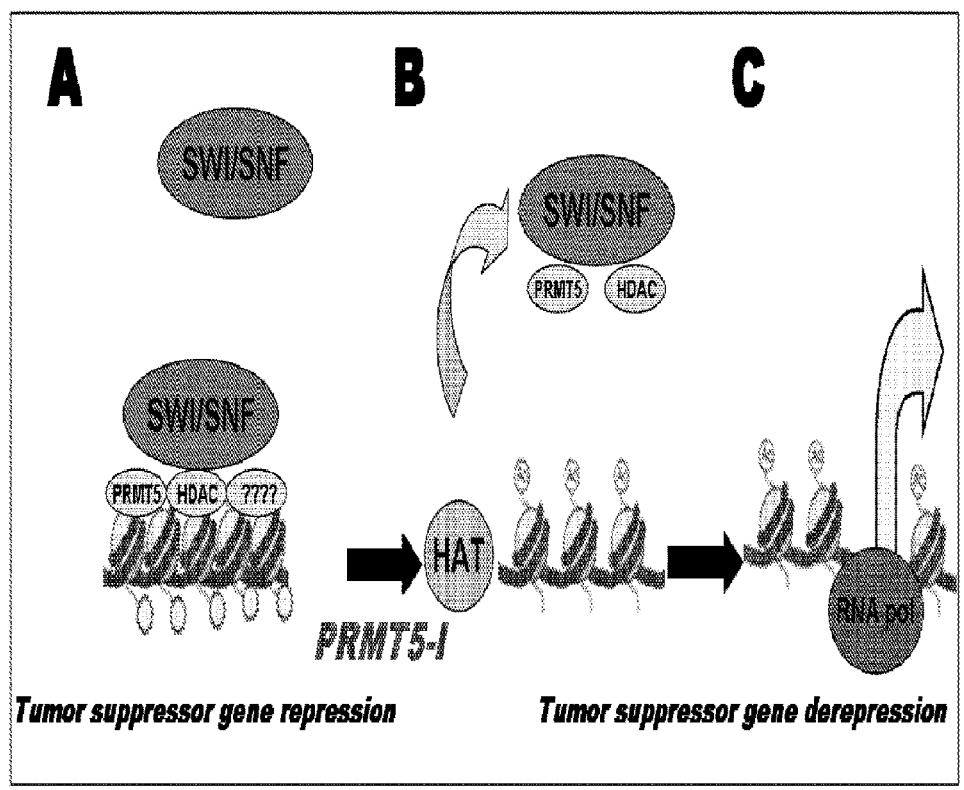
FIG. 1 shows epigenetic repression of anticancer genes and rationale for targeting PRMT5. (A) Both activating and repressive SWI/SNF complexes co-exist in the cellular proteome. Hypoacetylation of histones H3 and H4 promotes PRMT5-driven methylation of arginine residues resulting in condensed nucleosomal structure and repression of target tumor suppressor genes. (B) Following treatment with PRMT5 inhibitors, enzymes promoting gene expression are able to access chromatin and (C) restore expression of key regulatory genes.

The present inventions will now be described by reference to some more detailed embodiments, with occasional reference to the accompanying drawings. These inventions may, however, be embodied in different forms and should not be construed as limited to the embodiments set forth herein. Rather, these embodiments are provided so that this disclosure will be thorough and complete, and will fully convey the scope of the inventions to those skilled in the art.

Unless otherwise defined, all technical and scientific terms used herein have the same meaning as commonly understood by one of ordinary skill in the art to which these inventions belong. The terminology used in the description of the inventions herein is for describing particular embodiments only and is not intended to be limiting of the inventions. As used in the description of the inventions and the appended claims, the singular forms "a," "an," and "the" are intended to include the plural forms as well, unless the context clearly indicates otherwise. All publications, patent applications, patents, and other references mentioned herein are incorporated by reference in their entirety.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present inventions. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the inventions are approximations, the numerical values set forth in the specific examples are reported as precisely as possible. Any numerical value, however, inherently contains certain errors necessarily resulting from the standard deviation found in their respective testing measurements. Every numerical range given throughout this specification will include every narrower numerical range that falls within such broader numerical range, as if such narrower numerical ranges were all expressly written herein.

The expression "effective amount," when used to describe an amount of compound applied in a method, refers to the amount of a compound that achieves the desired pharmacological effect or other effect, for example an amount that inhibits the abnormal growth or proliferation, or induces apoptosis of cancer cells, resulting in a useful effect. The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

Contemplated herein are compounds of formula I:

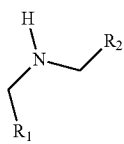
(I)

wherein
$R_1$ is

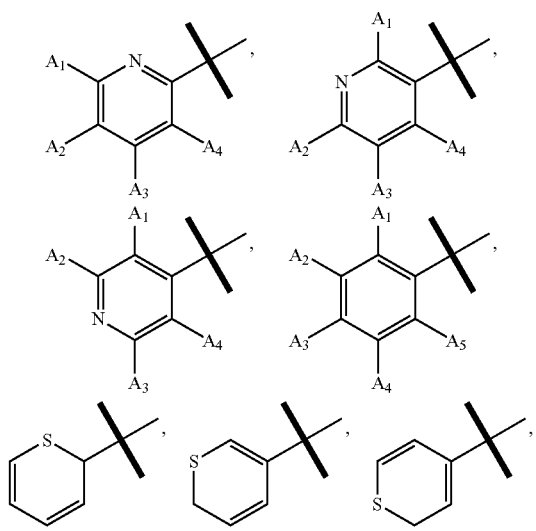

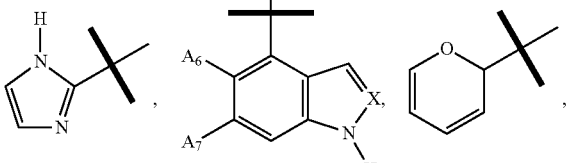

$R_2$ is

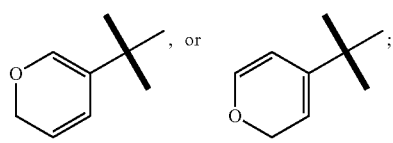

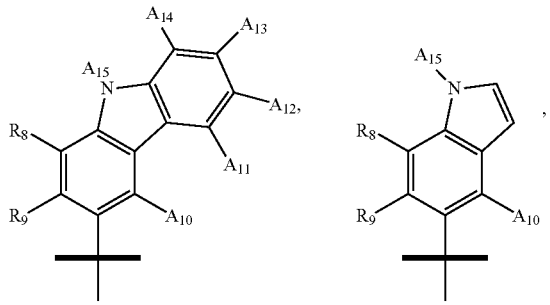

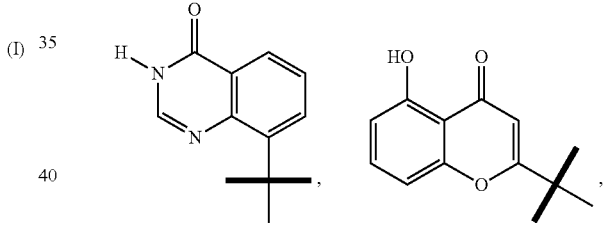

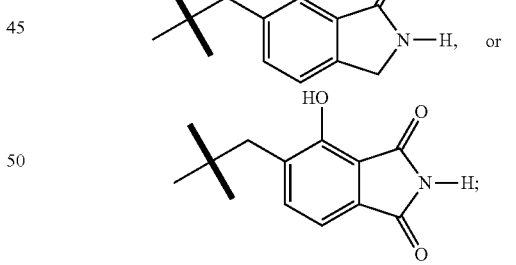

$A_1$, $A_2$, $A_3$, $A_4$, and $A_5$ are each individually hydrogen, halo, alkyl, alkoxyl, acetoxyl, alkylacetoxyl, —OH, trihalomethyl, —NH$_2$ or —NO$_2$;

$A_6$ and $A_7$ are each individually hydrogen, OH or NH$_2$;

$A_8$, $A_9$, $A_{10}$, $A_{11}$, $A_{12}$, $A_{13}$ and $A_{14}$ are each individually hydrogen, halo, alkyl, alkoxyl, acetoxyl, alkylacetoxyl, —OH, trihalomethyl, —NH$_2$ or —NO$_2$; and $A_{15}$ is alkyl (1-6 carbons in length); or a salt thereof. In some embodiments the compound of formula I may be

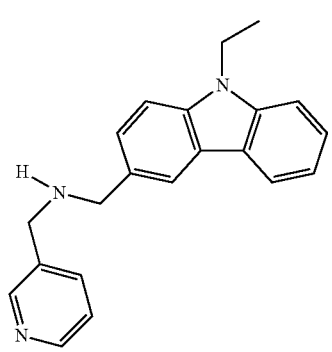 [SMILES: CCn1c2ccccc2c2cc(CNCc3cccnc3)ccc21]
Also contemplated herein are compounds of formula II
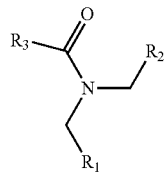 (II)
wherein
R₁ is
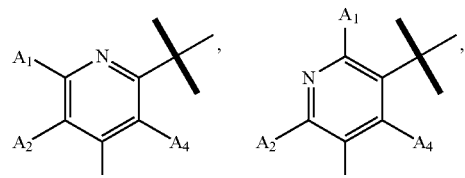
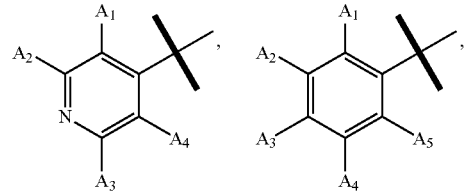
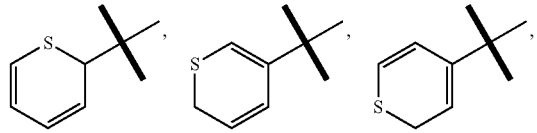
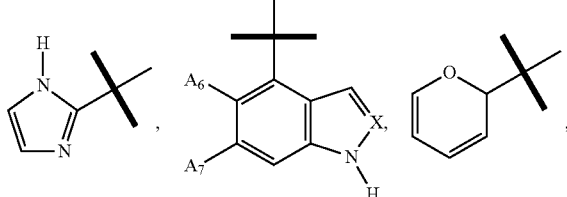
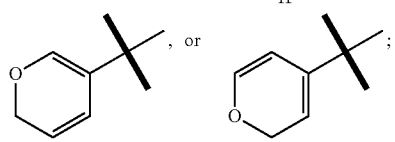
R₂ is
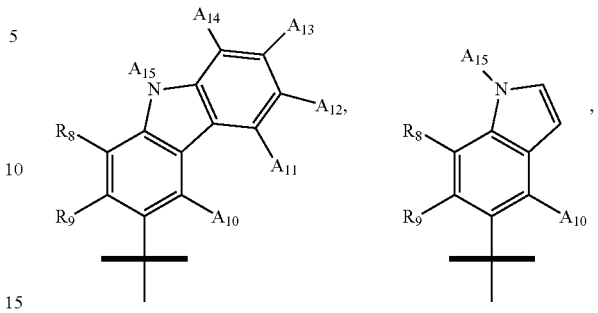
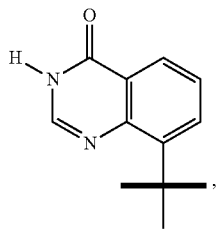 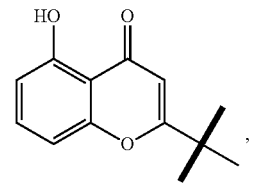
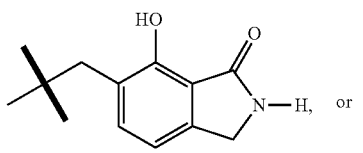
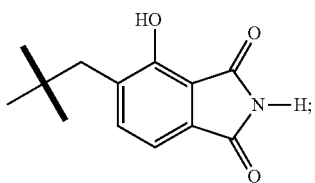
R₃ is
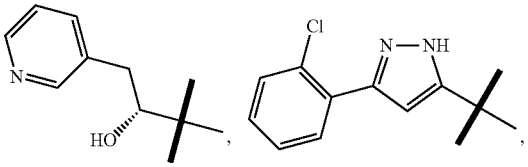
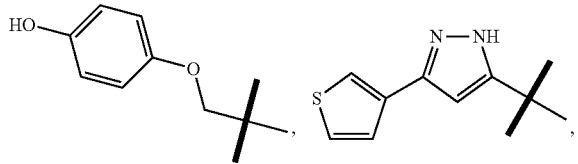
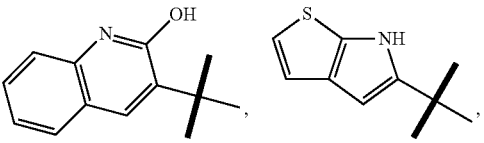

-continued

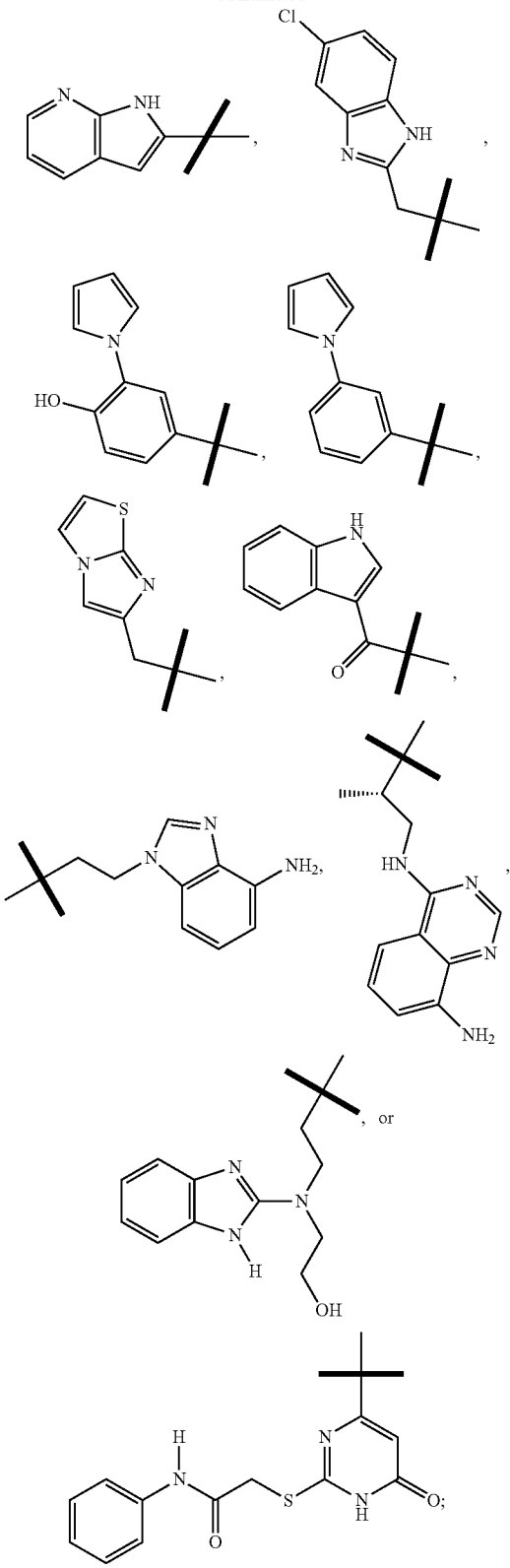

$A_1$, $A_2$, $A_3$, $A_4$, and $A_5$ are each individually hydrogen, halo, alkyl, alkoxyl, acetoxyl, alkylacetoxyl, —OH, trihalomethyl, —NH$_2$ or —NO$_2$;

$A_6$ and $A_7$ are each individually hydrogen, OH or NH$_2$;

$A_8$, $A_9$, $A_{10}$, $A_{11}$, $A_{12}$, $A_{13}$ and $A_{14}$ are each individually hydrogen, halo, alkyl, alkoxyl, acetoxyl, alkylacetoxyl, —OH, trihalomethyl, —NH$_2$ or —NO$_2$; and $A_{15}$ is alkyl (1-6 carbons in length); or a salt thereof. In some embodiments the compound may be

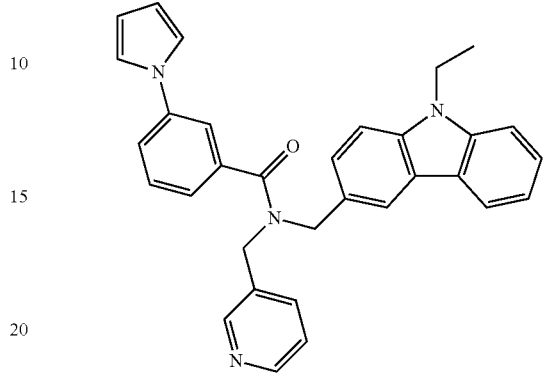

Also contemplated herein are pharmaceutical compositions comprising a therapeutically effective amount of the compound of formula (I) or compound of formula (II), in combination with a pharmaceutically suitable carrier.

The compounds according to formula I or II, any of the embodiments thereof, as well as intermediates used in making compounds according to formula I or II may take the form of salts. The term "salts" embraces addition salts of free acids or free bases which are compounds described herein. The term "pharmaceutically-acceptable salt" refers to salts which possess toxicity profiles within a range that affords utility in pharmaceutical applications. Pharmaceutically unacceptable salts may nonetheless possess properties such as high crystallinity, which may render them useful, for example in processes of synthesis, purification or formulation of compounds described herein. In general the useful properties of the compounds described herein do not depend critically on whether the compound is or is not in a salt form, so unless clearly indicated otherwise (such as specifying that the compound should be in "free base" or "free acid" form), reference in the specification to compounds of formula I or II should be understood as encompassing salts of the compound, whether or not this is explicitly stated.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, .beta.-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts.

All of these salts may be prepared by conventional means from the corresponding compound according to formula I or II by reacting, for example, the appropriate acid or base with the compound according to formula I or II. Preferably the salts are in crystalline form, and preferably prepared by crystallization of the salt from a suitable solvent. The person skilled in the art will know how to prepare and select suitable salts for example, as described in Handbook of Pharmaceutical Salts Properties, Selection, and Use By P. H. Stahl and C. G. Wermuth (Wiley-VCH 2002).

The compounds according to formula I or II, and salts thereof as well as intermediates used in making compounds according to formula I or IL and salts thereof may take the form of solvates, including hydrates. In general, the useful properties of the compounds described herein are not believed to depend critically on whether the compound or salt thereof is or is not in the form of a solvate.

The compounds according to formula I or II, and salts thereof as well as intermediates used in making compounds according to formula I or II, and salts thereof, may be administered in the form of prodrugs. By "prodrug" is meant for example any compound (whether itself active or inactive) that is converted chemically in vivo into a biologically active compound of the formula I or II following administration of the prodrug to a patient.

Generally a "prodrug" is a covalently bonded carrier which releases the active parent drug when administered to a mammalian subject. Prodrugs can be prepared by modifying functional groups present in the compounds in such a way that the modifications are cleaved, either in routine manipulation or in vivo, to the parent compounds. Prodrugs include compounds wherein hydroxyl, amino, sulfhydryl, or carboxyl groups are bonded to any group that, when administered to a mammalian subject, cleaves to form a free hydroxyl, amino, sulfhydryl, or carboxyl group respectively. Examples of prodrugs include, but are not limited to, acetate, formate and benzoate derivatives of alcohol and amine functional groups in the compounds according to formula I or II. Specifically, conjugates such as β-glucuronides and fl-galactosides have been suggested as prodrugs of hydroxamates. See Thomas, et al., Bioorg. Med. Chem. Lett., 2007, 983-986.

The suitability and techniques involved in making and using prodrugs are well known by those skilled in the art. Preparation and use of prodrugs is discussed in T. Higuchi and V. Stella, "Pro-drugs as Novel Delivery Systems," Vol. 14 of the ACS Symposium Series, and in Bioreversible Carriers in Drug Design, ed. Edward B. Roche, American Pharmaceutical Association and Pergamon Press, 1987, both of which are hereby incorporated by reference in their entirety.

The compounds of formula I or II may be administered in the form of a pharmaceutical composition, in combination with a pharmaceutically suitable carrier. The active ingredient in such formulations may comprise from 0.1 to 99.99 weight percent. "Pharmaceutically suitable carrier" means any carrier, diluent or excipient which is compatible with the other ingredients of the formulation and not deleterious to the recipient.

The active agent may be administered with a pharmaceutically suitable carrier selected on the basis of the selected route of administration and standard pharmaceutical practice. The active agent may be formulated into dosage forms according to standard practices in the field of pharmaceutical preparations. See Alphonso Gennaro, ed., Remington: The Science and Practice of Pharmacy, 20th Edition (2003), Mack Publishing Co., Easton, Pa. Suitable dosage forms may comprise, for example, tablets, capsules, solutions, parenteral solutions, troches, suppositories, or suspensions.

The specific dose of a compound according to formula I or II required to obtain therapeutic benefit in the methods of treatment described herein will, of course, be determined by the particular circumstances of the individual patient including the size, weight, age and sex of the patient, the nature and stage of the disease being treated, the aggressiveness of the disease disorder, and the route of administration of the compound.

Compounds according to formula I or II are therapeutically useful. There are therefore provided uses of the compounds according to formula I or II in therapy and diagnostics, and therapeutic and diagnostic methods comprising administering a compound according to formula I or II, or a pharmaceutically acceptable salt thereof, to an individual.

Also contemplated herein are compositions comprising compounds of formula I or II and HDAC inhibitors.

The compounds according to formula I or II are believed effective against a broad range of cancers and tumor types, including but not limited to bladder cancer, brain cancer, breast cancer, colorectal cancer, cervical cancer, gastrointestinal cancer, genitourinary cancer, head and neck cancer, lung cancer, ovarian cancer, prostate cancer, renal cancer, skin cancer, and testicular cancer. More particularly, cancers that may be treated by the compounds, compositions and methods described herein include, but are not limited to, the following: cardiac cancers, including, for example sarcoma, e.g., angiosarcoma, fibrosarcoma, rhabdomyosarcoma, and liposarcoma; myxoma; rhabdomyoma; fibroma; lipoma and teratoma; lung cancers, including, for example, bronchogenic carcinoma, e.g., squamous cell, undifferentiated small cell, undifferentiated large cell, and adenocarcinoma; alveolar and bronchiolar carcinoma; bronchial adenoma; sarcoma; lymphoma; chondromatous hamartoma; and mesothelioma; gastrointestinal cancer, including, for example, cancers of the esophagus, e.g., squamous cell carcinoma, adenocarcinoma, leiomyosarcoma, and lymphoma; cancers of the stomach, e.g., carcinoma, lymphoma, and leiomyosarcoma; cancers of the pancreas, e.g., ductal adenocarcinoma, insulinoma, glucagonoma, gastrinoma, carcinoid tumors, and vipoma; cancers of the small bowel, e.g., adenocarcinoma, lymphoma, carcinoid tumors, Kaposi's sarcoma, leiomyoma, hemangioma, lipoma, neurofibroma, and fibroma; cancers of the large bowel, e.g., adenocarcinoma, tubular adenoma, villous adenoma, hamartoma, and leiomyoma; genitourinary tract cancers, including, for example, cancers of the kidney, e.g., adenocarcinoma, Wilm's tumor (nephroblastoma), lymphoma, and leukemia; cancers of the bladder and urethra, e.g., squamous cell carcinoma, transitional cell carcinoma, and adenocarcinoma; cancers of the prostate, e.g., adenocarcinoma, and sarcoma; cancer of the testis, e.g., seminoma, teratoma, embryonal carcinoma, teratocarcinoma, choriocarcinoma, sarcoma, interstitial cell carcinoma, fibroma, fibroadenoma, adenomatoid tumors, and limphoma; liver cancers, including, for example, hepatoma, e.g., hepatocellular carcinoma; cholangiocarcinoma; hepatoblastoma; angiosarcoma; hepatocellular adenoma; and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull, e.g., osteoma, hemangioma, granuloma, xanthoma, and osteitis defoinians; cancers of the meninges, e.g., meningioma, meningiosarcoma, and gliomatosis; cancers of the brain, e.g., astrocytoma, medulloblastoma, glioma, ependymoma, germinoma (pinealoma), glioblastoma multiform, oligodendroglioma, schwannoma, retinoblastoma, and congenital tumors; and cancers of the spinal cord, e.g., neurofibroma, meningioma, glioma, and sarcoma; gynecological cancers, including, for example, cancers of the uterus, e.g., endometrial carcinoma; cancers of the cervix, e.g., cervical carcinoma, and pre tumor cervical dysplasia; cancers of the ovaries, e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma; cancers of the vulva, e.g., squamous cell carcinoma, intraepithelial carcinoma, adenocarcinoma, fibrosarcoma, and melanoma; cancers of the vagina, e.g., clear cell carcinoma, squamous cell carcinoma, botryoid sarcoma, and embryonal rhabdomyosarcoma; and cancers of the fallopian tubes, e.g., carcinoma; hematologic cancers, including, for example, cancers of the blood, e.g., acute myeloid leukemia, chronic myeloid leukemia, acute lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis; and adrenal gland cancers, including, for example, neuroblastoma.

The compounds according to formula I or II can also be administered in combination with existing methods of treating cancers, for example by chemotherapy, irradiation, or surgery. Thus, there is further provided a method of treating cancer comprising administering an effective amount of a compound according to formula I or II, or a salt thereof, to an individual in need of such treatment, wherein an effective amount of at least one further cancer chemotherapeutic agent is administered to the individual. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

The compounds may be administered by any route, including oral, rectal, sublingual, and parenteral administration. Parenteral administration includes, for example, intravenous, intramuscular, intraarterial, intraperitoneal, intranasal, intravaginal, intravesical (e.g., to the bladder), intradermal, transdermal, topical or subcutaneous administration. Also contemplated is the instillation of a drug in the body of the patient in a controlled formulation, with systemic or local release of the drug to occur at a later time. For example, the drug may be localized in a depot for controlled release to the circulation, or for release to a local site of tumor growth. Advantageously, the compounds are administered in the form of a pharmaceutical composition.

In another aspect, there is provided a method for predicting the susceptibility of a cancer to treatment with PRMT5 inhibitors comprising contacting a cancer cell with a PRMT5 inhibitor, comparing the distribution of PRMT5 in the cell after contacting with the distribution of PRMT5 in the cell before contacting or the distribution of PRMT5 in a control cell which has not been contacted with the compound to determine whether the contacting with the compound results in an increase in the relative concentration of PRMT5 in the cytoplasm of the cell as compared to the nucleus of the cell.

EXAMPLES

High Grade Gliomas Overexpress PRMT5 and is Inversely Related to Survival

Figure 2:
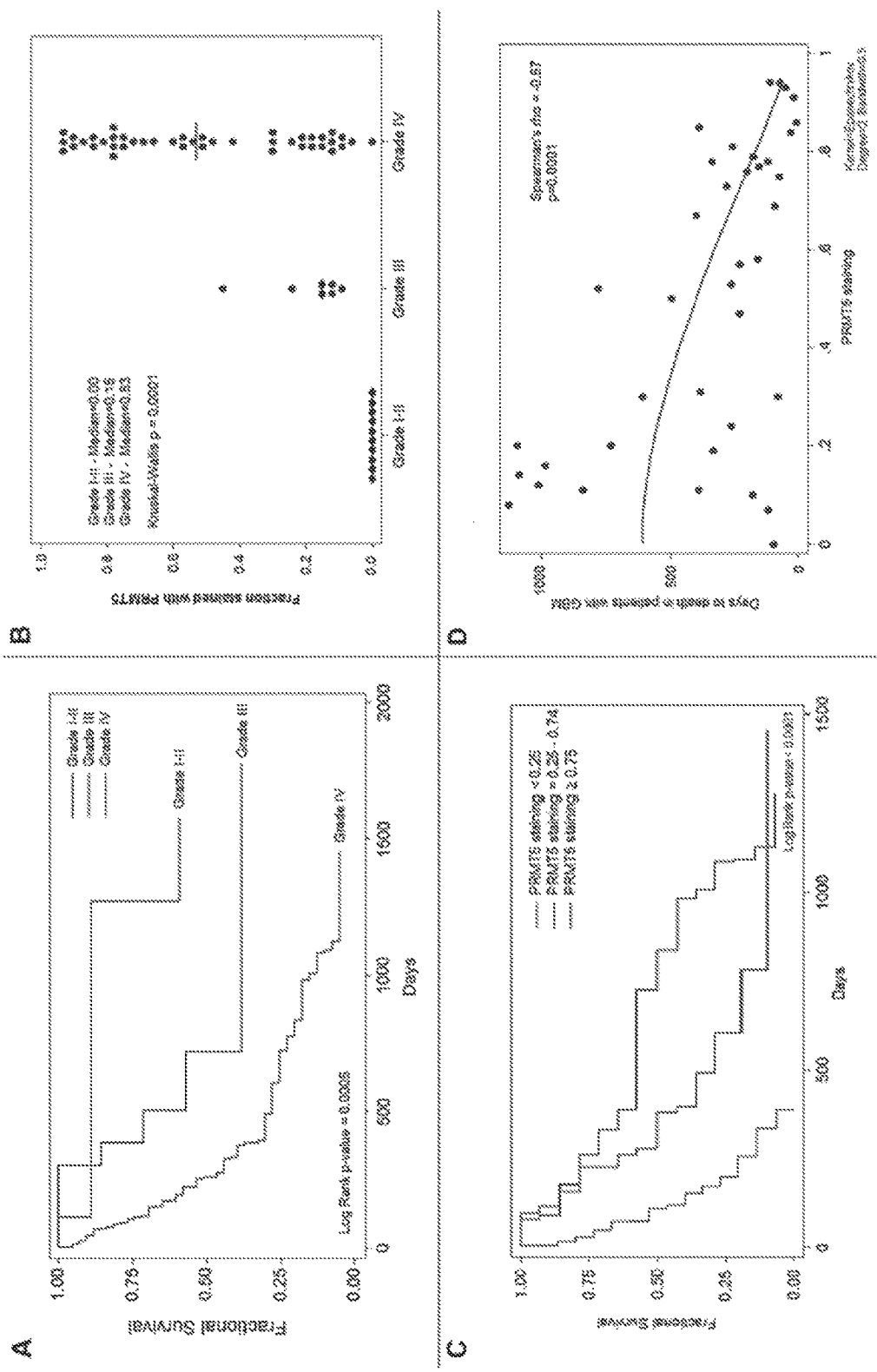
FIG. 2 shows PRMT5 is overexpressed in GBM and is inversely correlated with survival (A) Kaplan Meier plots of overall survival by glioma grade. As expected, glioma grade is significantly associated with overall survival in the cohort. (B) Distribution of PRMT5 expression level by glioma grade. PRMT5 levels are significantly associated with glioma grade (Kruskal-Wallis equality-of-populations rank test p=0.0001). (C) Kaplan Meier plots of overall survival by PRMT leve in GBM. In patients with GBM there was a statistically significant association of PRMT5 level and overall survival (Log rank p<0.0001). (D) Time to death and PRMT5 level in patients who died with GBM. PRMT5 level is continuously associated with time to death (Spearman's rho=−0.57, p=0.0001).

It has been demonstrated that epigenetic processes driven by PRMT5 overexpression are relevant in regulation of key oncogenic pathways that are operable in B-cell lymphomas and GBM. Eight patient-derived GBM cell lines and 45 GBM tumors express abundant levels of PRMT5 protein. Interestingly, no low or intermediate grade astrocytomas expressed PRMT5 suggesting that PRMT5 overexpression may play a pathologic role selectively in high-grade astrocytomas. Importantly, normal brain or normal human astrocytes did not express any measurable PRMT5. In support of this, PRMT5 expression inversely correlated with survival of GBM patients (FIG. 2, r=−0.57, p=0.0001) and correlated with proliferation rate of GBM cell lines (not shown, r=0.81, p<0.0001). Elevated PRMT5 expression is also observed in the GBM tumors of symptomatic mice in a preclinical mouse model of GBM. Previous studies showed that PRMT5 can stimulate cell growth and proliferation and induce transformation, cells that overexpressed PRMT5 were able to form colonies at a rate comparable to that of MYC/RAS-transformed cells (10). These results indicate that PRMT5 could be a potential oncogenic marker and therapeutic target for primary and recurrent GBM.

Inhibition of PRMT5 Overexpression Leads to Apoptosis, Cell Cycle Arrest, and Reduced Invasiveness of GBM Cell Lines.

Figure 3:
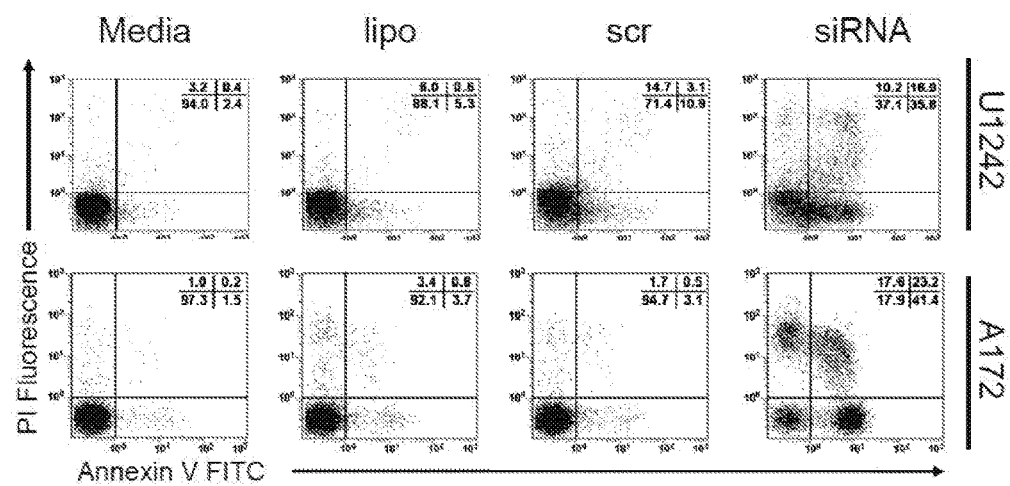
FIG. 3 shows (A) Inhibition of PRMT5 with siRNA (48 hrs) overexpression in GBM cell lines (U1242 p53 mut, A172 p53 wt) results in apoptosis as measured by annexin V PI staining and flow cytometry. (B) inhibition of migration at 12 hrs after addition of siRNA to knock down PRMT5 vs. Scramble siRNA control.
Figure 3:
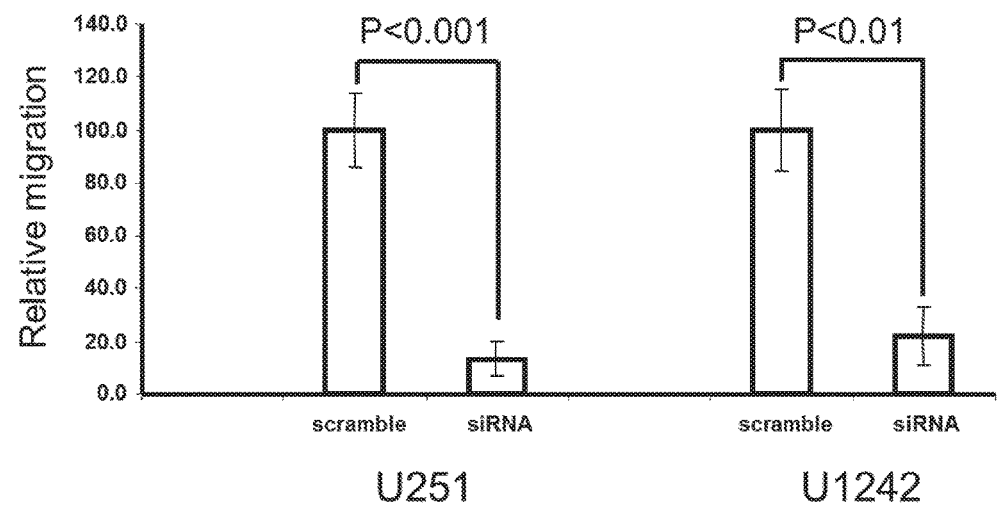

We developed small inhibitory RNA molecules (siRNA) that efficiently knock-down PRMT5 expression leading to demethylation of target histone protein arginine residues (H4R3). SiRNA specific for PRMT5 led GBM cells to undergo cell cycle arrest (not shown), spontaneous apoptosis and complete inhibition of cell migration (FIG. 3). PRMT5 silencing displayed a significant increase in the Bax/Bcl-2 ratio relative to the ratio observed in the scramble control, validating the role of the up regulation of Bax in PRMT5 silencing induced apoptosis. Apoptosis occurred independent of caspase enzyme activity and p53 status. PRMT5 siRNA46: TGCCTATGAACTCTTTGCC; PRMT5 siRNA5: ATAGCTGACACACTAGGGG; PRMT5 siRNA48: TCTCAGACATATGAAGTGT; PRMT5 siRNA-D: CCGCTATTGCACCTTGGAA.

Our results showed that PRMT5 silencing substantially reduced invasiveness of GBM cells by transwell assay (FIG. 3B), scratch assay also showed that migration of GBM cells significantly decreased with PRMT5 silencing. Other preliminary data showed PRMT5 to be over expressed in the GBM-like tumors of p53/pten/Nf1 haploinsufficient mice that has become an interesting preclinical model of GBM. PRMT5 knockdown led GBM cell lines to become markedly sensitized to the toxic effects of temazolomide, an agent with antitumor activity in GBM primary tumors and in brain tumor stem cells that give rise to GBM.

Tumor Suppressor Gene ST7 and Chemokines RANTES, IP10, CXCL11 are Targeted and Silenced by PRMT5.

Figure 4:
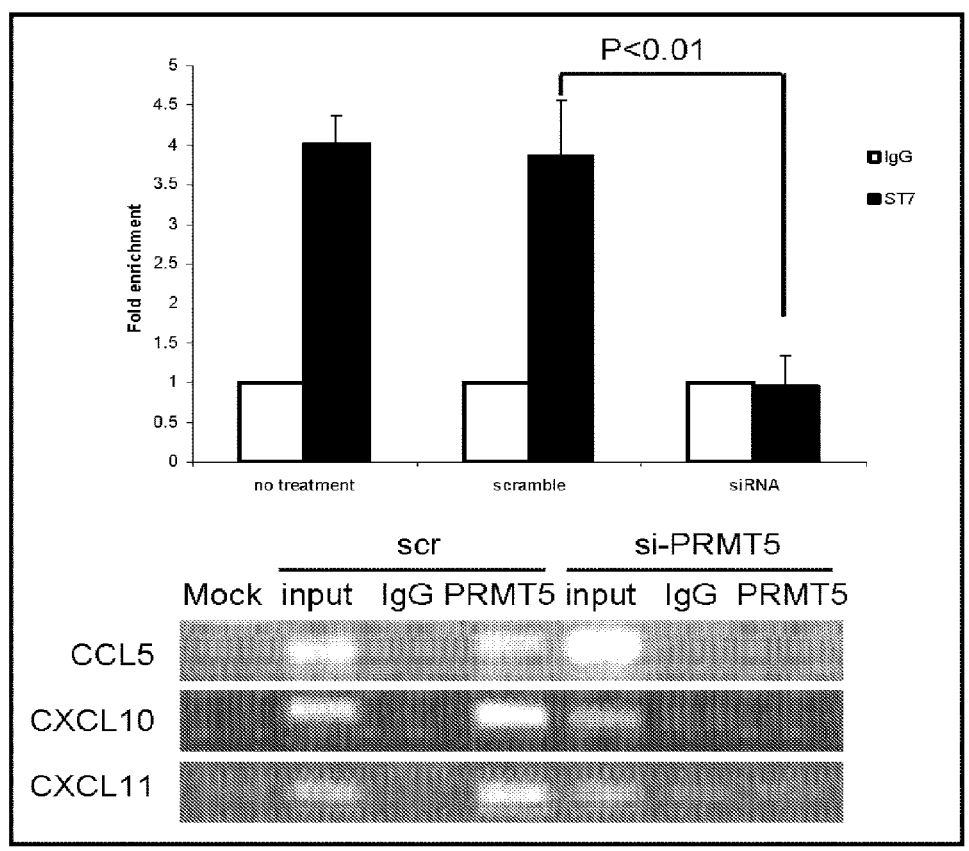
FIG. 4 shows quantitative/qualitative PCR results using primers that specifically amplify promoter regions of ST7 and Chemokines CCL5, CXCL10 and CXCL11.

We used a microarray to identify potential targets of PRMT5, TSG ST7 and three chemokines (RANTES, IP10, CXCL11) were identified to be targets of PRMT5. Chromatin immunoprecipitation assay showed that siRNA treatment led to loss of PRMT5 recruitment on the promoter of the ST7, RANTES, IP10, and CXCL11. FIG. 4 shows quantitative/qualitative PCR results using primers that specifically amplify promoter regions of ST7 and Chemokines CCL5, CXCL10 and CXCL11. Treatment of cells with siRNA to knock down PRMT5 levels shows that ChIP assays fail to amplify promoter regions indicating loss of PRMT5 recruitment on each of the examined promoters.

Figure 5:
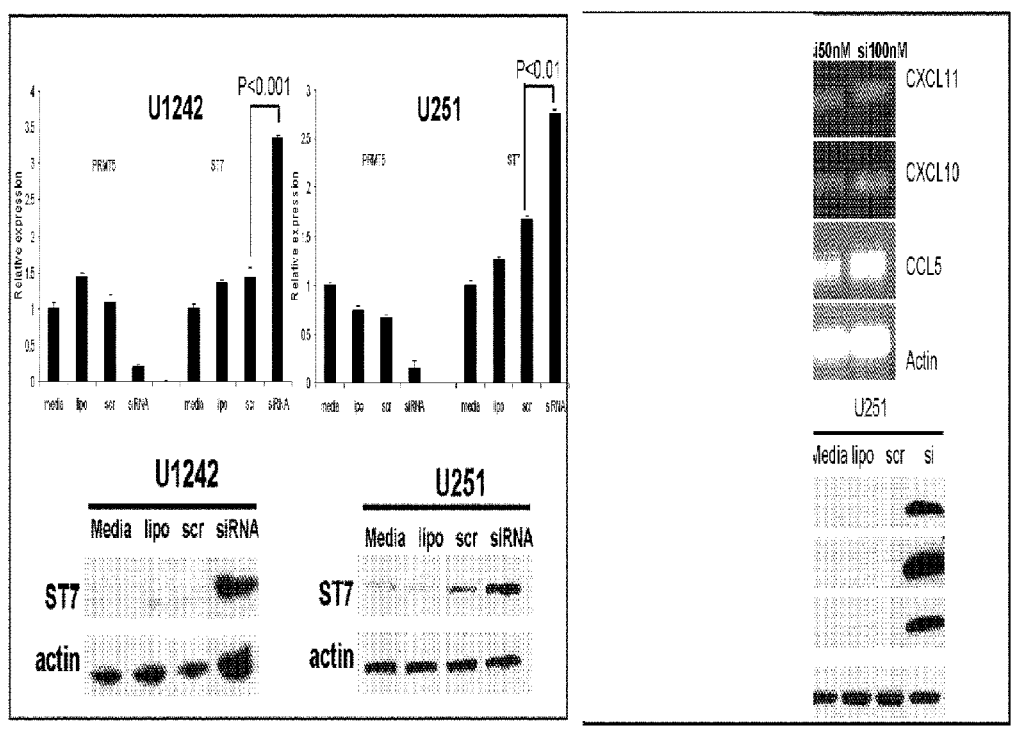
FIG. 5 shows siRNA knockdown of PRMT5 leads to increased ST7 and Chemokine transcription as measured by real time quantitative PCR (left top panels) and qualitative PCR (right top panel). Western blot analysis shows that this increased transcription results in enhance protein expression of the ST7 tumor suppressor and immune modulatory chemokines CCL5, CXCL10 and CXCL11 (left and right bottom panels, respectively).

ST7, RANTES, IP10, and CXCL11 transcript and protein levels rapidly increased after PRA/ITS silencing FIG. 5. PRMT5 knockdown led to secretion of the chemokines into medium, which might help to recruit NK cells and T cells to elicit immune response toward GBM tumors. The human ST7 gene was first recognized as a candidate tumor suppressor based on its chromosomal location (7q31.1) at a site of frequent loss of heterozygosity and its reduced expression in some types of cancer. ST7 induces remodeling of the extracellular matrix in other solid tumors indicating that ST7 mediates tumor suppression by changing the tumor microenvironment which may contribute to inhibition of invasiveness and migration of human GBM cells by PRMT5 silencing. Collectively, our data suggest that PRMT5 silencing may be an attractive strategy to explore alone and in combination with other agents that target epigenetic processes.

Comparative Modeling of Human PRMT5 and Model Validation by Molecular Docking.

siRNA technology is in the beginning stages of development. The first phase 1 study was completed with a small micro RNA in 2009 and, while the technology represents a promising advance for future experimental therapeutic strategies, other approaches to inhibit PRMT5 activity would certainly be more attractive. We therefore explored rational design of small molecule compounds to inhibit PRMT5 activity. We constructed an "in silico" model since PRMT5 crystal structure has not been described. A model of human PRMT5 catalytic domain was built from available homologous crystal structures. The hPRMT5 sequence retrieved from NCBI sequence database (NP_006100; 637 aa) was submitted as query for protein BLAST to PDB database using NCBI blastp. Out of the several hits, four unique templates which had approximately 40-50% similarity to the human sequence were selected for modeling (Table 1). The template structures were co-crystallized with SAH, the catalytic reaction product. One of the crystal structures of rat PRMT1 (PDB ID: 1OR8) was co-crystallized with a peptide arginine residue also along with SAH.

TABLE 1

BLAST result for the selected templates for human PRMT5 modeling.

| PDB ID | Protein | Organism | Identity | Similarity | Gaps | Alignment |
|--------|---------|----------|----------|------------|------|-----------|
| 2V74 | CARM1 | Mouse | 28 | 44 | 8 | 329-483 |
| 2FYT | PRMT3 | Human | 21 | 38 | 16 | 324-598 |
| 1F3L | PRMT3 | Rat | 21 | 39 | 14 | 324-598 |
| 1OR8 | PRMT1 | Rat | 26 | 48 | 7 | 359-475 |

The model building and refinement was carried out with MODELLER9v1 (Sali and T. L. Blundell, 1993). Structure-based sequence alignment verified the highly conserved nature of this domain, especially the amino acids closest to the catalytic site. The residues directly participating in the catalytic function were primarily located towards the N-terminal half of the catalytic domain. The automodel optimization and refinement protocol in Modeller was used to generate 100 models with SAH in the catalytic site. In this protocol, each model is initially optimized with the variable target function method (VTFM) with conjugate gradients. It is further refined using molecular dynamics with simulated annealing protocol. Best model based on the built-in energetic criterion was selected for structure-based virtual screening.

Structural super-positioning of the selected templates to the model showed that the tertiary structure is essentially conserved although the sequence identity is low. This is to be expected since all the proteins have similar function and uses the same co-factor (SAM) for catalytic function. A visual inspection of the aligned catalytic site of the templates revealed that the key catalytic interactions are conserved in the model as well. This include Glu392 involved in the bifurcated hydrogen bonding with ribose hydroxyl groups of the co-factor SAM and the Glu435 involved in hydrogen bonding with arginine of the histone substrate.

Figure 6:
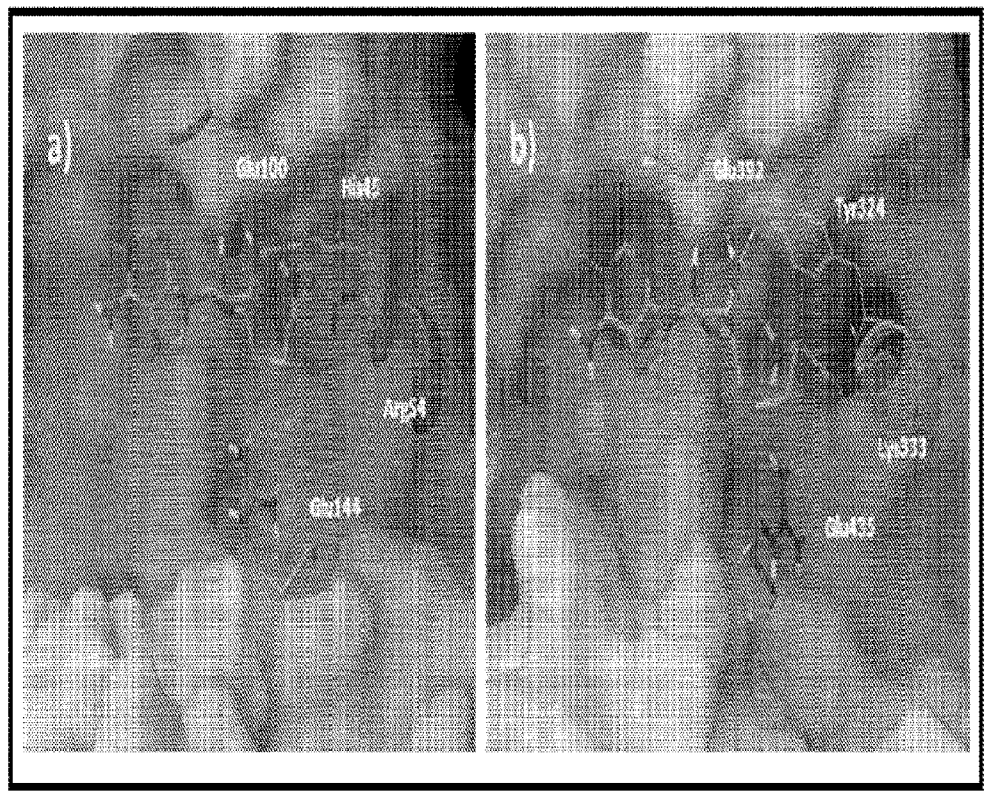
FIG. 6 shows SAH and arginine residue conformations docked to Human PRMT5 model (b) as compared to crystal structure rat PRMT1 (PDB ID: 1OR8) with co-crystallized SAH and substrate arginine (a). For clarity, protein molecular surface is generated omitting the residues covering the catalytic site face. Surface transparency is applied to show catalytic residues. Conserved catalytic residue interactions are reproduced in docking to hPRMT5 model as displayed. Glu392 makes bifurcated hydrogen bonding with ribose hydroxyl groups whereas the substrate arginine residue hydrogen bonds with Glu435.

The final model from Modeller was taken into Schrodinger molecular modeling environment Maestro v8.5 for preliminary preparation for docking employing the recommended Protein Preparation Wizard protocol. Proper protonation states and hydrogen bonding network within the protein was optimized. The structure was minimized using imperf program with cut off criteria of 0.30 A RMSD using OPLS2005 force field. The final structure was carried forward for the docking experiments. A grid cube box of 25 Å size was created around the model keeping the SAH as the center. A van der Waal's scaling of 0.9 was used in the protein grid preparation in order to account for the soft induced fit effect. In order to validate the modeled active site, the non-selective PRMT inhibitor sinefungin and SAH were docked flexibly into the model using GLIDE XP in Schrodinger suite 2008. The docking result essentially reproduced the crystal mode as compared by superimposing the bioactive SAH crystal structure from its native crystal structure. (FIG. 4) The SAH docked human PRMT model was then used to generate a grid for another docking calculation to probe the close-by substrate arginine binding site. Docking with capped arginine residue could reproduce similar interactions as observed in the template crystal co-ordinate (FIG. 6). These molecular docking experiments confirmed that the catalytic site was modeled appropriately to screen larger library of compounds to find potential competitive enzyme inhibitors.

Virtual Screening.

The validated docking protocol was used to screen ChemBridge CNS-Set™ screening library of 10,000 compounds. The compound library digital version in 2D SDF file format was submitted to a ligand coordinate preparation protocol employing LigPrep program. LigPrep accounts for the different tautomeric and stereoisomeric states of the compounds as well as a low energy ring conformation sampling. Possible ionization states of the compounds at pH 7±2 were generated using Ionizer module. Final coordinates were minimized by OPLS2001 molecular mechanics force field to obtain geometry optimized 3D coordinates. The prepared library of 17,090 coordinates was screened through the HTVS (High Throughput Virtual Screening) stage of the Virtual Screening Workflow script provided with the Schrodinger suite 2008. Non-planar amide bond conformations were penalized in all the stages of the docking run. The retained 50% of the top scored coordinates were then passed to the second stage of SP (Standard Precision) screening. The top 50% of the coordinates were finally screened by the most rigorous calculation in the XP (Extra Precision) stage. All the scored coordinates in this stage were retained for further investigation.

Compounds with lowest binding energy from the screen were visually inspected for contacts that mimic conserved PRMT-SAH-ARG interactions. A set of constraints; the requirement of ligand binding occupancy at a) the co-factor binding pocket and b) at the substrate arginine-PRMT binding cavity; were used in the compound selection. Eight potential compounds were identified for biological investigation based on their binding energy as listed in the table above (FIG. 7) Compound 5 (binding energy: −8.10 kcal/mol) is shown docked into the hPRMT5 model (pink carbon, ball and stick representation). SAH (green carbon) and capped arginine residue (red carbon; only side chain visible) docked binding positions from the model validation docking experiments are superimposed as line representation. For clarity, protein molecular surface is generated omitting the residues covering the catalytic site face. Hydrogen bonds to the protein are shown in yellow dotted lines.

Initial Screening of Compounds in Bioassays.

Figure 9:
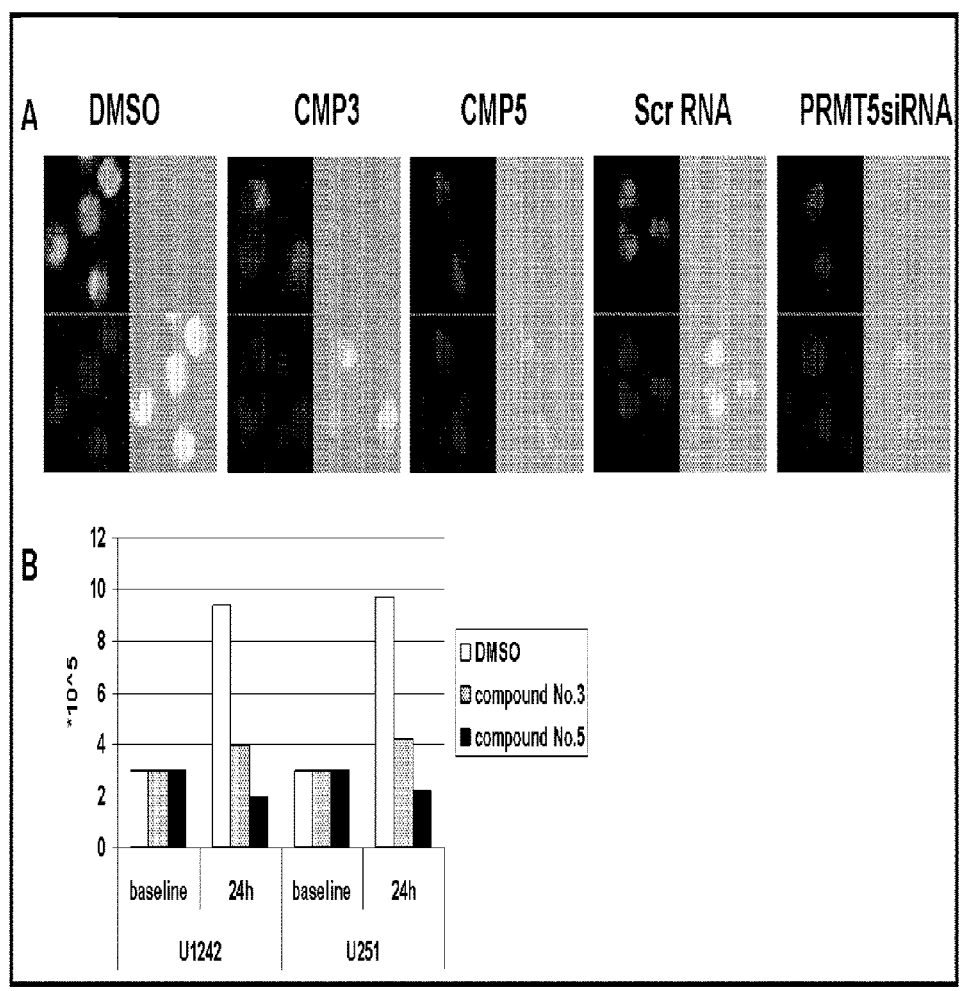
FIG. 9 shows (A) Comparison of symmetric 2Me arginine methylation on H4R3 residues following a 8 hour incubation of the glioma cell line U1242 with compounds 3 and 5. Confocal microscopy was used with mAbs specific for symmetrical dimethylation (S2Me) of histone H4R3. Positive control for loss of PRMT5 activity was provided by treatment of U1242 cells with a PRMT5-specific siRNA used in above experiments. (B) Cell proliferation was assessed in replicate cultures incubated in DMSO and compounds 1-8. Compounds 3 and 5 were the only compounds that resulted in reduced cell proliferation and H4R3 S2Me. All other compounds showed proliferation rates comparable to DMSO control conditions.

Initial Screening experiments were performed utilizing monoclonal antibodies specific for H4R3 symmetric dimethyl arginine and confocal microscopy generated images evaluating H4R3 methylation. Controls included scrambled and SiRNA specific for PRMT5 to verify knockdown and loss of H4R3 methylation. Confocal images in FIG. 9 show that Compounds 3, 5, and 8 (not shown) were capable of inhibiting H4R3 symmetric 2Me arginine methylation similar to that seen with SiRNA based inhibition of PRMT5 expression. Initial dose titration of these compounds revealed that these compounds also possessed similar anti proliferative activity (FIG. 7B) and promote apoptosis of GBM cell lines (not shown). Findings similar to PRMT5-specific SiRNA treatment. Interestingly, none of the remaining 5 compounds in our screen (FIG. 7), all of which failed to change the symmetrical dimethylation (S2Me) of H4R3, had any toxic or anti proliferative activity on GBM cells. This observation suggested that the reduction in S2Me of H4R3 (and thus PRMT5 activity) correlated with an anticancer activity that we've observed with SiRNA specific for PRMT5.

Figure 10:
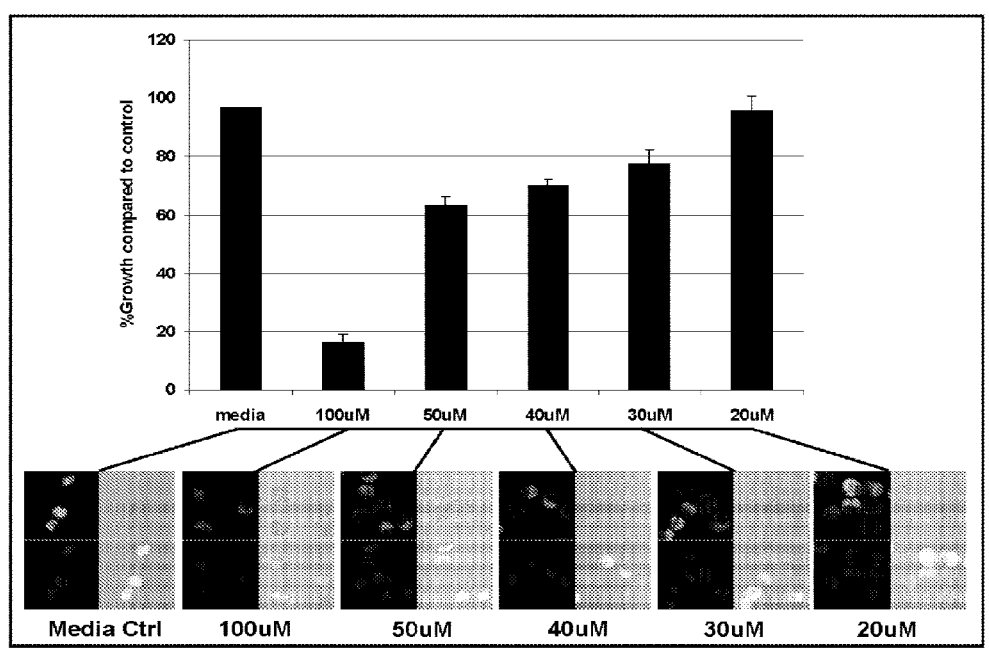
FIG. 10 shows absolute cell numbers determined at 48 hours after addition of either control or various concentrations of compound 5 identified in the initial screen. Top figure is cell growth compared to control and bottom panel shows S2Me-H4R3 content in each condition.

Compound 5 appeared to demonstrate the most efficacy in blocking both S2Mc of the PRMT5 target H4R3 and proliferation of the U1242 cell line. Therefore, we performed a series of titration experiments with compound 5 to evaluate if a dose response was observed at both degree of reduced S2Me and proliferation rate. Following addition of DMSO media control or compound 5 (20 uM, 30 uM, 40 uM, 50 uM and 100 uM). FIG. 10 shows absolute cell numbers determined at 48 hours after addition of either control or various concentrations of compound 5 identified in our initial screen. Interestingly, a dose response was seen at both cellular proliferation and the degree of H4R3 methylation. Compound 5 was therefore chosen as our lead compound around which we would direct our focus on verifying selectivity of PRMT5 enzyme inhibition as well as future strategies to enhance its potency and activity against high grade glioma tumors. Preliminary enzymatic activity assays are currently underway and will be provided as an update during submission of supplementary materials.

Figure 11:
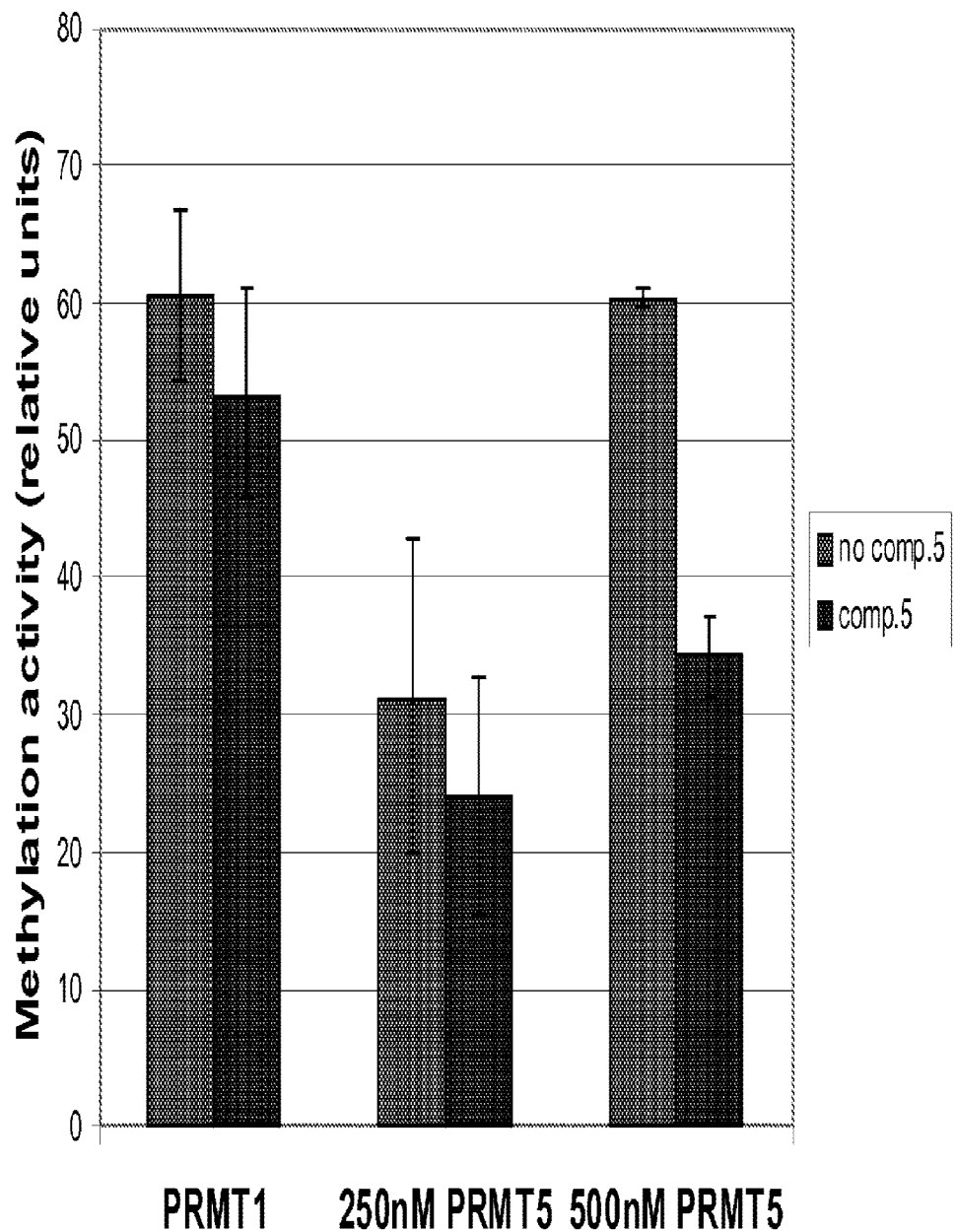
FIG. 11 shows that compound 5 was capable of selectively inhibiting PRMT5 activity (and not PRMT1 activity). This demonstrates that the inhibitors demonstrate selective type II PRMT inhibition.

After determining that compound 5 demonstrated the best activity (by inhibition of S2M3-H4R3), we next wished to explore whether compound 5 was capable of selectively inhibiting a type II PRMT enzyme. Do achieve this, we performed enzyme inhibition assays using purified PRMT1 (a type I PRMT enzyme) and purified PRMT5 (a type II PRMT enzyme). We were able to demonstrate in 3 replicate experiments, that compound 5 was capable of selectively inhibiting PRMT5 activity (and not PRMT1 activity FIG. 11, p<0.0001).

Inhibiting PRMT5 with Compound 5 is Improved with HDAC Inhibition.

Figure 12:
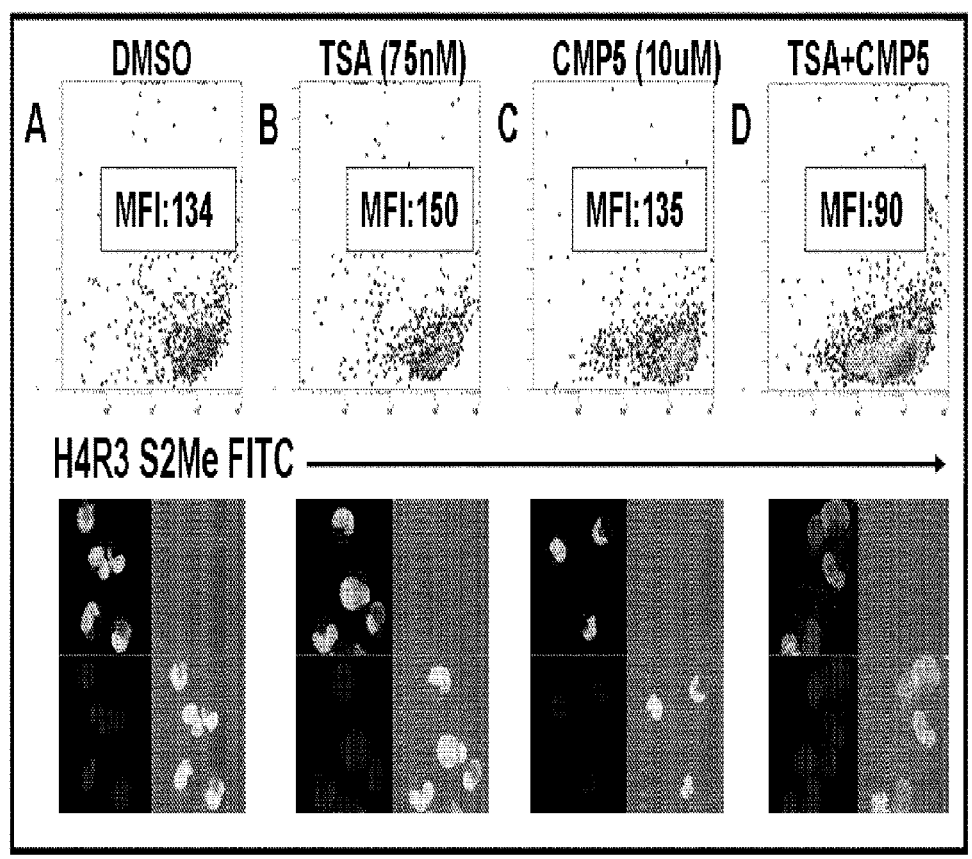
FIG. 12 shows U1242 GBM cells were treated with (A) DMSO control, (B) HDAC inhibitor TSA (75 uM), (C) CMP5 (10 uM), or (D) combination TSA+CMP5. Cells were stained with a mAb specific for symmetrical dimethyl arginine H4R3 and evaluated by flow cytometry (top panels) and confocal microscopy (bottom). This figure demonstrates loss of S2Me H4R3 with low concentrations of CMP5 and HDAC inhibitor TSA consistent with biochemical synergy allowing CMP5 to inhibit PRMT5 more efficiently at low concentrations when in the presence of HDACi.

Recent work reported by Pal et al has shown that PRMT5 associates with SWI/SNF chromatin remodeling complexes along with other co-repressor molecules like HDAC2. Biochemical assays have demonstrated that PRMT5 activity on target H4R3 and H3R8 histone arginine residues is markedly enhanced when lysine residues become deacetylated by HDAC enzymes. We therefore wished to sec if we could achieve improved PRMT5-inhibitory activity by co-treating GBM cell lines with low doses of HDAC inhibitors (TSA, 75, 100 nM) that have been shown to result in acetylation of lysine residues neighboring PRMT5 target arginine residues. FIG. 12 shows the results of these studies. We were able to achieve loss of S2Me status of H4R3 at much lower (>10-fold) concentrations of compound 5 (10 uM) when cells were co-treated with the HDACi TSA. We utilized a flow cytometric assay to evaluate symmetric dimethyl H4R3 (S2Me-H4R3) content and confocal microscopy to verify loss of methylation status. Anti tumor activity is also enhanced when PRMT5 inhibitors are used in combination with HDAC inhibitor drugs.

Generating More Potent PRMT5 Inhibitors.

To generate more potent and selective small molecule compounds to inhibit PRMT5 activity. The ability to achieve equivalent or improved enzyme inhibition at much lower concentrations will likely enhance specificity of our reagent while minimizing the likelihood of toxicity during preclinical evaluation in our in vitro and in vivo development platforms.

Figure 13:
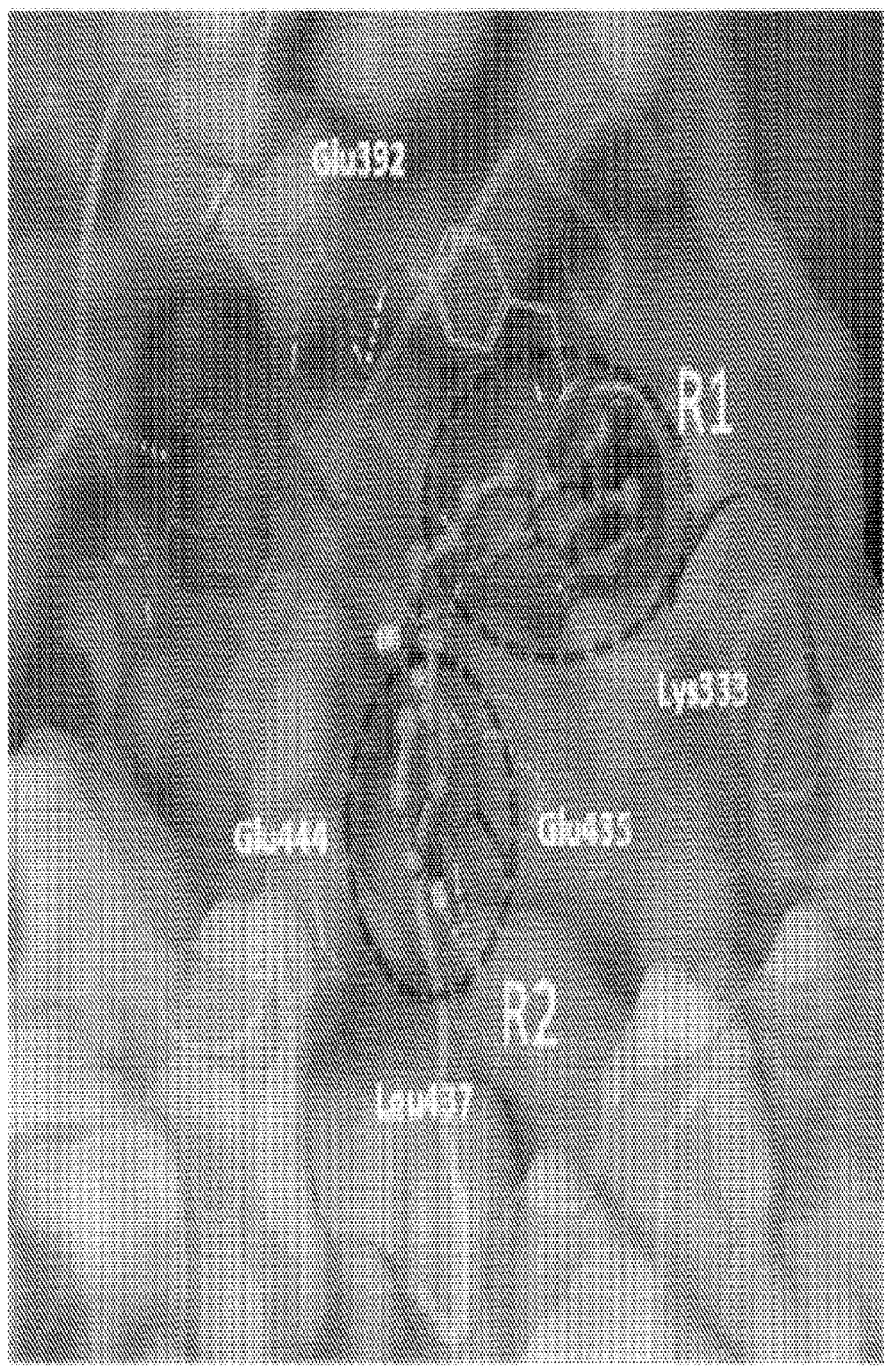
FIG. 13 shows Compound 5 (ChemBridge ID 9033823; pink carbon, stick representation) docked to the hPRMT5 model (binding energy: −8.10 kcal/mol) over laid with docked SAH (Green carbon, line representation) and. The tricyclic ring system (R1) fits to the pocket making favorable van der Waal's interaction and cation-pi interaction with the conserved amino acid residue Lys333. The substrate Arginine binding pocket (R2) is occupied by the pyridine ring.

These experiments utilized compound 5 as the "backbone compound" and modification of R groups to allow for various permutations that will enhance inhibitory activity and potency (FIG. 13). Consequently, these experiments initially produced additional candidate compounds for evaluation. It may be necessary to further optimize compounds to allow for improved bio availability, CNS blood brain barrier penetration, or reduced toxicity. A combination of structure based computational efforts and synthetic medicinal chemistry approaches will be used to continue our search for an optimal compound. The computationally selected candidates will be synthesized and evaluated for biological activity. Compound 5 is commercially available; however, the synthetic scheme of the compound has never been reported. We synthesized compound 5 through a one step reductive amination reaction. All the optimized analogs can be synthesized with the similar procedure as compound 5.

Computational Optimization of Lead Compound 5.

Two similar approaches will be used for the structure based lead compound optimization; 1) AlleGrow uses a grow algorithm on the binding site utilizing a pre-assigned chemical fragment library, 2) CombiGlide uses commercially available synthetic reagent library. The binding features of the lead compound 5 (ChemBridge ID 9033823) shows key favorable van der Waal's, aromatic, cation-pi and H-bonding interactions to the hPRMT5 catalytic site (FIG. 13).

Figure 14:
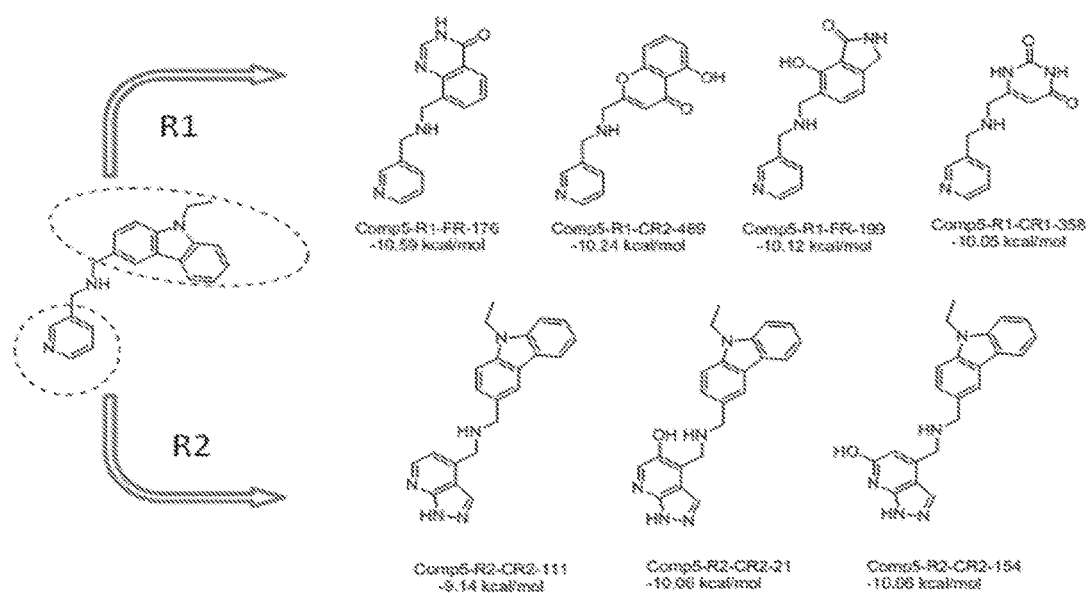
FIG. 14 shows 7 potential compounds with improved binding energies have been determined and are identified for chemical synthesis.

Preliminary combinatorial optimization of the lead compound 5 using AlleGrow already identified a few novel derivatives with Glide XP scoring energies about 1-3 kcal/mol stronger in binding than the lead compound itself. Keeping R2 fixed, several ring structures were substituted for R1 and their binding affinity were evaluated using Glide XP. Similarly, R1 was fixed and R1 substitution chemical space was explored. Out of the several tens of thousands of combinations evaluated, 7 potential compounds with improved binding energies have been determined and are identified for chemical synthesis. (FIG. 14). Additional compounds with equivalent binding energies have been designed and synthesized and are presently under evaluation.

Figure 15:
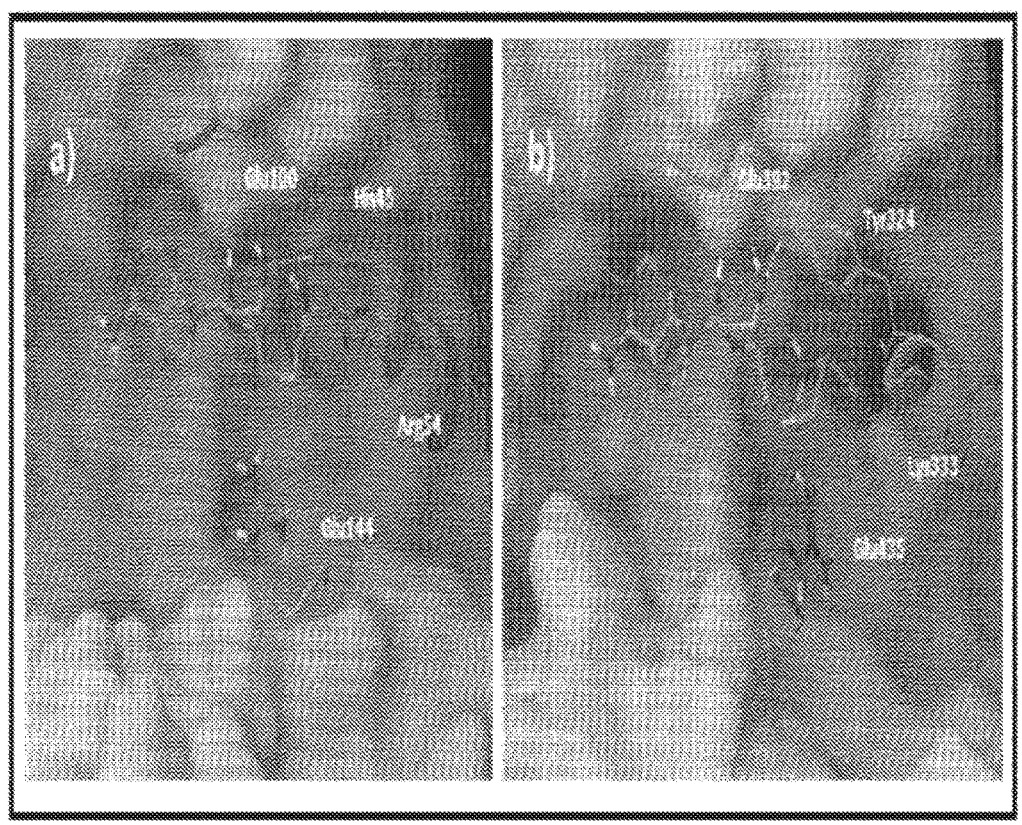
FIG. 15 shows virtual compounds docked to the catalytic site to evaluate the binding energy.

A larger and diverse synthetic chemical space are presently being computationally explored by utilizing commercially available chemical library. Schrodinger CombiGlide program will be used for this approach. A comprehensive database of commercially available compounds is provided free for academic use by UCSF (ZINC; zinc.docking.org). Current version of ZINC (v 8.0) database contains more than 8 million compounds. The fragment like subset of ZINC currently stores 453,539 compounds. The reagent files prepared from these compound fragments will be combinatorially attached to R1 and R2 substitution positions respectively to generate several hundreds of thousands of compounds. These virtual compounds are docked to the catalytic site to evaluate the binding energy (FIG. 15). Several compounds with better energy compared to the original compound 5 have been selected for chemical synthesis and biological evaluation FIG. 14). Combinatorially optimized novel R2 substituted compounds in the binding pocket (FIG. 15b) as compared to the binding of compound 5, SAH and substrate arginine residue (FIG. 15a). R2 Optimized compounds with enhanced binding affinity show additional hydrogen bonding to Glu444 carboxylate oxygen and Leu437 backbone carbonyl oxygen.

Characterization of PRMT5 Enzyme Inhibition with Lead Compound 5 (CMP5).

Figure 8:
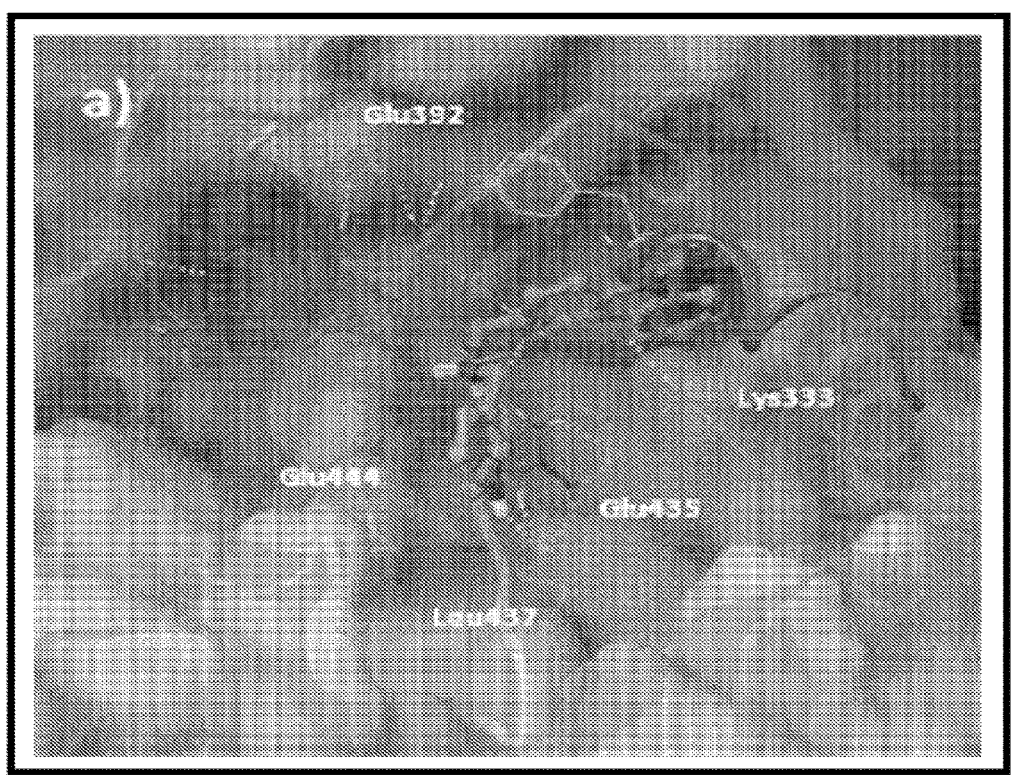
FIG. 8 shows a binding pocket where compound 5 (CMPZ5) (from FIG. 7) fits into the active site and blocks interaction between SAH and the arginine binding pocket.
Figure 16:
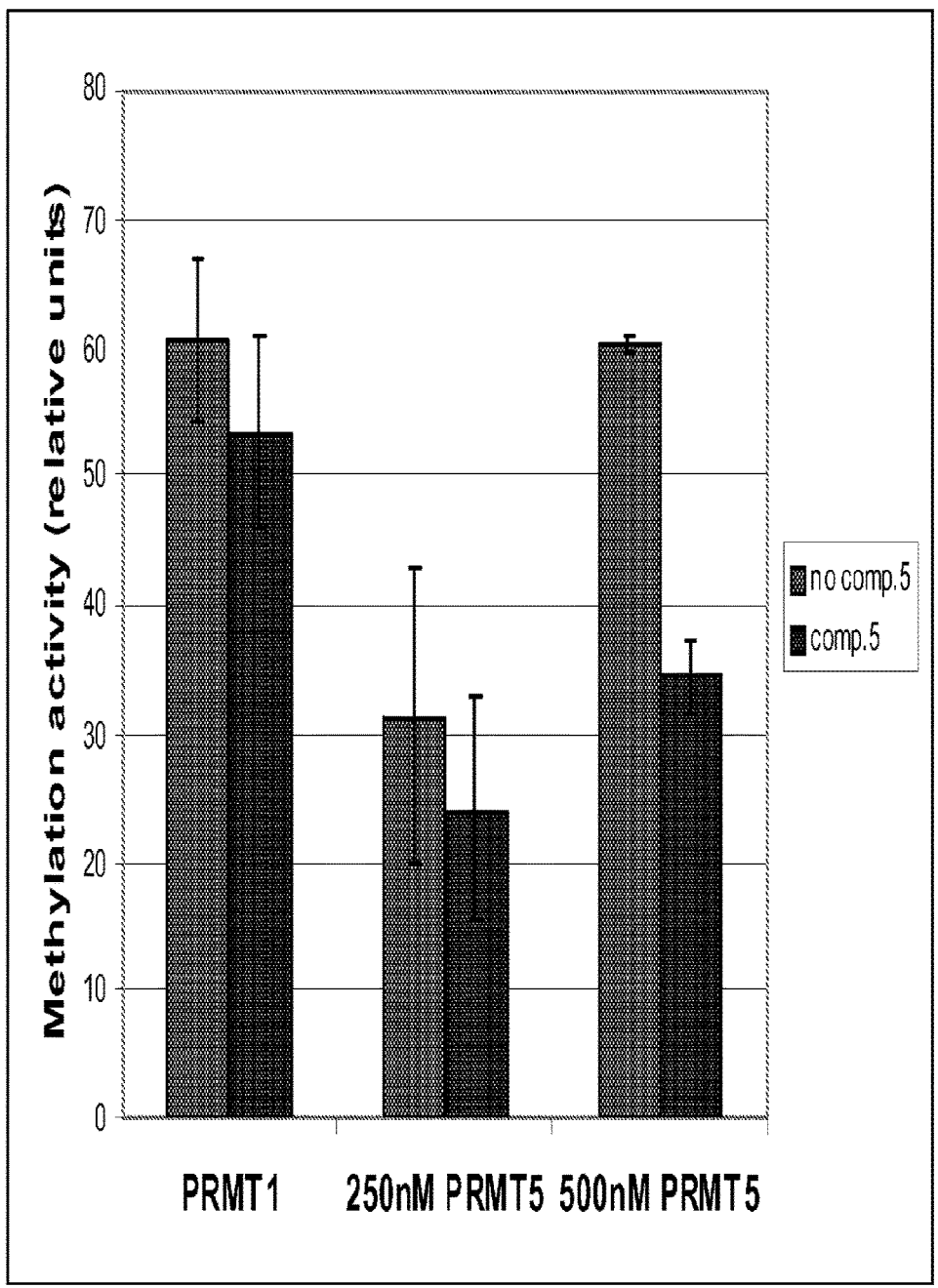
FIG. 16 shows that CMP5 was capable of selectively inhibiting PRMT5 activity and not PRMT1 enzymatic activity.

The screening of our first candidate compounds identified by our PRMT5 in silico model showed CMP5 to have the most profound effects as demonstrated by loss of symmetric dimethyl-H4R3 and antiproliferative effect in astrocytoma cells (FIGS. 7 & 8). The next step required studies to explore whether CMP5 was capable of selectively inhibiting a type II PRMT enzyme. Type I PRMT enzymes are involved in transcriptional activation (asymmetric dimethylation at H4R3) and type II PRMT enzymes regulates transcriptional repression (symmetric dimethylation or S2Mc at H4R3). To achieve this goal, we performed enzyme inhibition assays using purified PRMT1 (type I PRMT enz) and purified PRMT5 (type II PRMT enz). Assays were performed utilizing 2 methods. The first utilized methods described previously by Zhao et at (Nat Struct Mol Biol. 2009), where 1 ug of H4 (Roche) was used as substrate and 2 uCi of S-adenosyl-L-methyl-$^3$H-methionine ($^3$H-SAM; Amersham) as the methyl donor in the presence or absence of 100-500 uM of CMP5 was incubated in HMTase buffer for 3 h at 37° C. Reaction mixtures were spotted on Whatman P-81 filter paper and washed to remove unincorporated [$^3$H]SAM. Methylated peptides were detected by scintillation counting. This method showed significant inhibition of methyltransferase activity (55% reduction±7.8%, p<0.001, data not shown). The second method utilized a methyltransferase activity assay to distinguish if differential inhibitory activity of CMP5 existed against the type I PRMT1 vs. the type II enzyme PRMT. The methyltransferase assay we used (Amsbio inc) utilized purified PRMT5 and PRMT1 enzyme preparations and tested for methylation of Histone H4 at arginine 3 (H4R3). SAM was incubated with a sample containing substrate H4 peptide, different concentrations of methyltransferase enzymes (PRMT5 or PRMT1), in presence or absence of CMP5 (100-500 uM) for one hour at 37° C. Fluorescently labeled SAM tracer was added followed by anti-SAM antibody that produces a change in fluorescent polarization that can be measured using a fluorescence reader. We were able to demonstrate in 3 replicate experiments, that CMP5 was capable of selectively inhibiting PRMT5 activity and not PRMT1 enzymatic activity (FIG. 16, p<0.0001). Because of the differential activities of these two distinct classes of PRMT enzymes, the outcome of our inhibitor experiments has important implications. We know that PRMT5 is selectively over expressed in high grade astrocytomas (FIG. 2), works to silence both tumor suppressor genes and proinflammatory cytokines, and is directly involved with promoting malignant cell growth and survival. Discovery of a small molecule inhibitor with selective type II PRMT enzyme inhibitory activity at low micro molar range, has allowed us to now direct our focus on improving the potency and selectivity of our lead compound (CMP5). It has also allowed us to pursue studies investigating anti tumor activity of this compound (below).

Design and Synthesis of a Second Generation of CMP5 Analogs (BLL2-BLL8).

Figure 17:
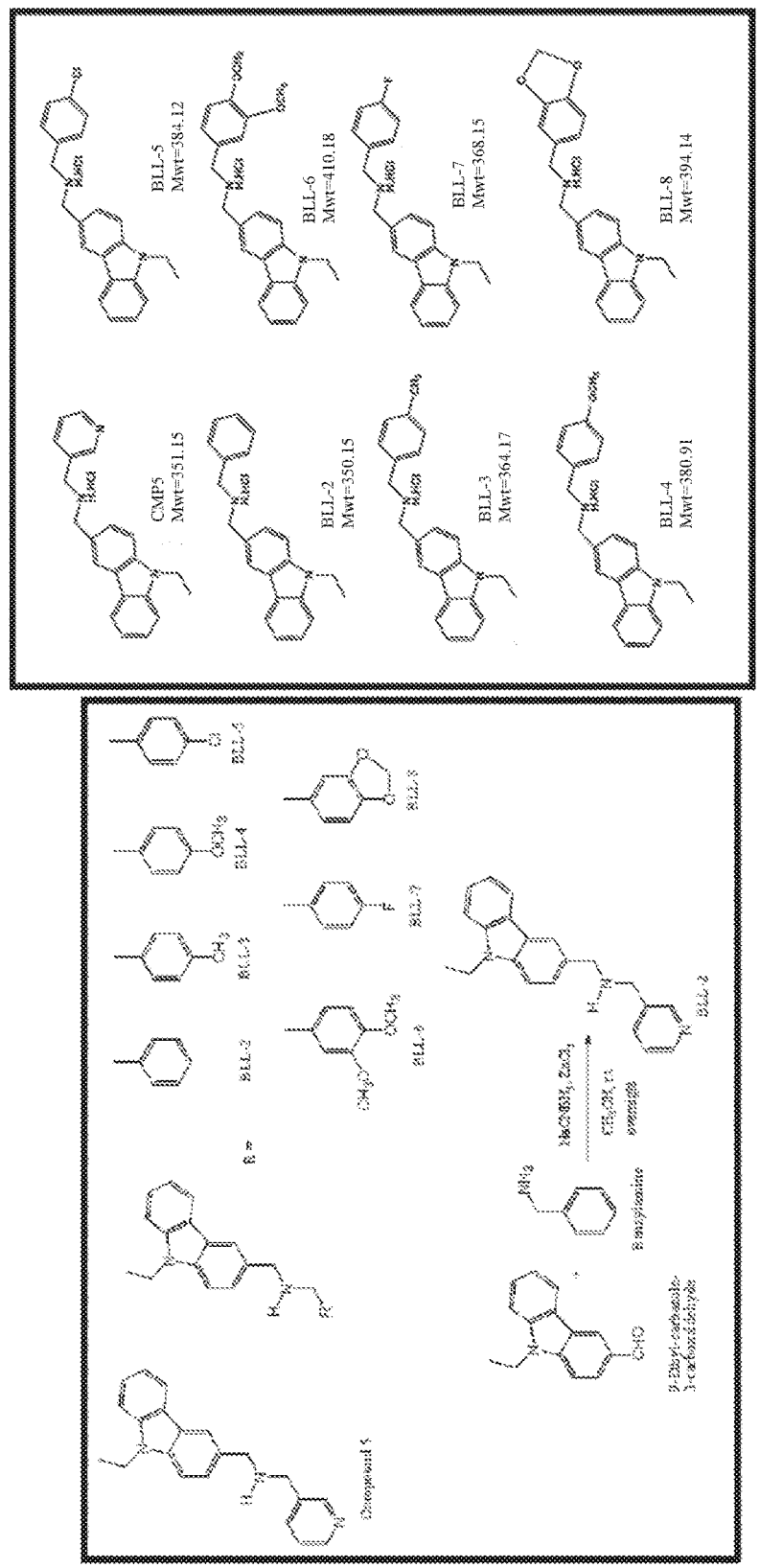
FIG. 17 shows the design of the analogs is based on replacing the pyridine ring of CMP5 with different substituted benzene. BLL-2-BLL-8 were synthesized through a one step reductive amination reaction.

Specific Aim 1 of our proposal outlines a strategy to design and synthesize compounds with more potent and selective PRMT5 inhibitory activity. We have designed and synthesized 7 additional analogs of CMP5 (BLL2-BLL8). The design of the analogs is based on replacing the pyridine ring of CMP5 with different substituted benzene. BLL-2-BLL-8 were synthesized through a one step reductive amination reaction (FIG. 17) similar to the synthesis of CMP5. Presently we have synthesized mg quantities of CMP5 (BLL1) and BLL 2-8 and are now screening for selective PRMT5 (vs PRMT1) inhibitory activity in our bioassays and methyltransferase enzyme assays.

PRMT5 Inhibition and Anti Tumor Activity is Enhanced when Used in Combination with Histone Deacetylase (HDAC) Inhibitors.

Figure 18:
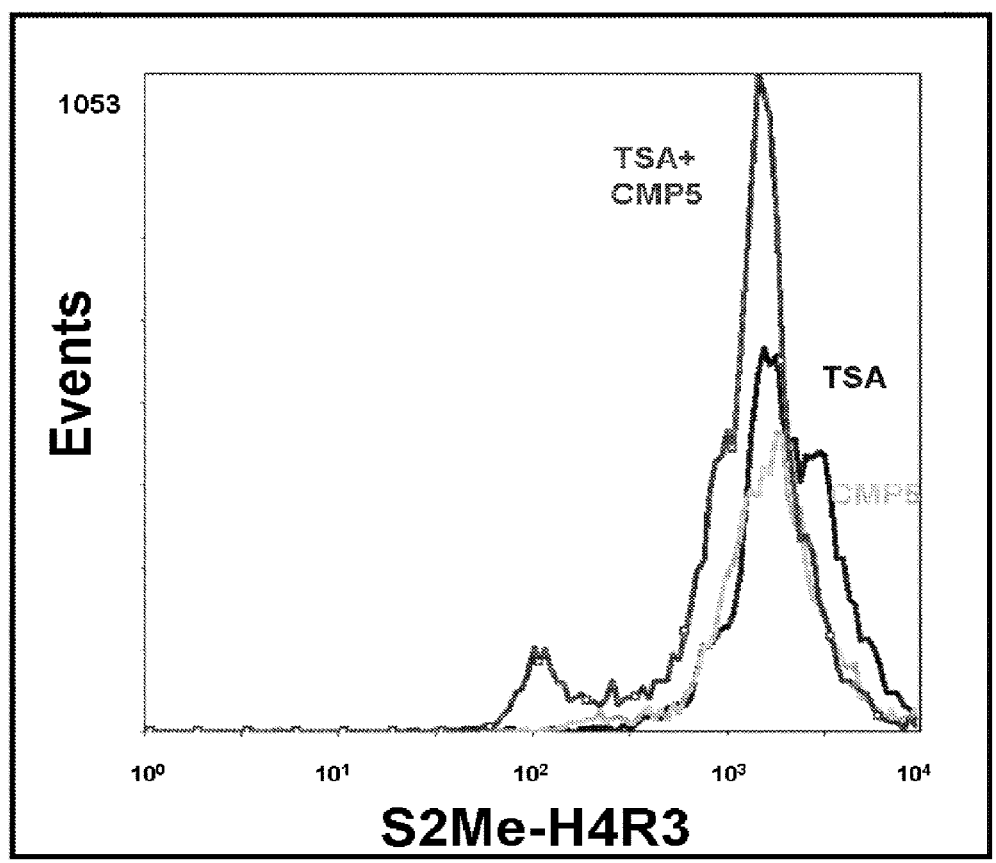
FIG. 18 shows use of single agent CMP5 (green) or TSA (blue) showed no change in S2Me-H4R3, however combination treatment (red) showed significant loss of methylation.
Figure 19:
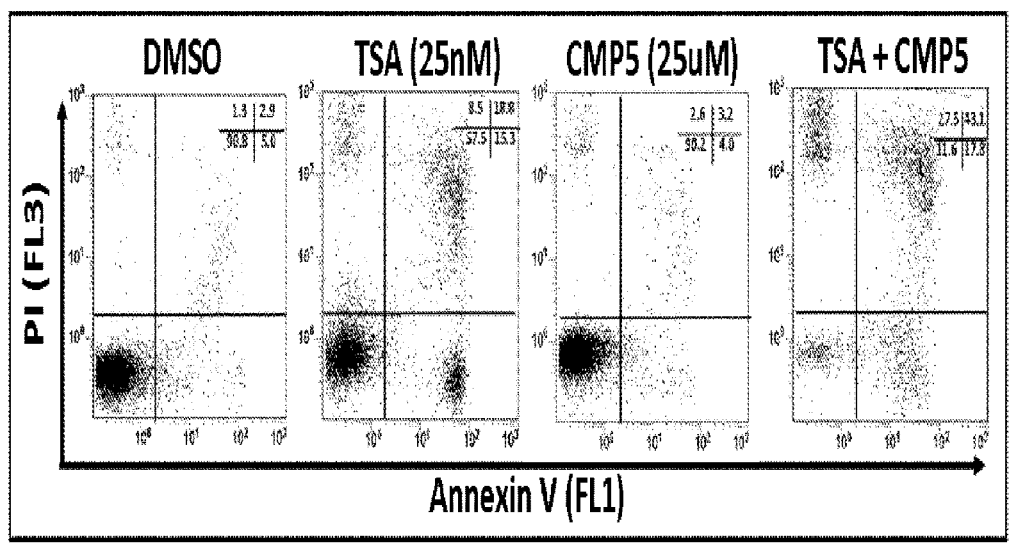
FIG. 19 shows anti tumor, proapoptotic activity was enhanced in a synergistic fashion when low dose CMP5 was used in combination with the HDAC inhibitor TSA.

The biochemical association of PRMT5 and HDAC2 with repressive chromatin remodeling complexes and cooperative enzyme kinetics has been previously described. FIG. 9 shows that S2Mc-H4R3 is unchanged in astrocytoma cell lines treated with single agent HDAC inhibitor (TSA) or CMP5 (PRMT5 inhibitor at 25 uM), however, when drugs are combined, the reduction of S2Me at H4R3 occurred in a synergistic fashion. Importantly, these results were achieved at concentrations of CMP5 that are log fold lower compared to our original dose response experiments where 100 uM CMP5 was required for reduced methylation (see FIG. 8). To evaluate the consequences of this enhanced loss of S2Me-H4R3 on histone 4, we performed an evaluation of cellular apoptosis at 24, 48 and 72 hours after plating astrocytoma cell lines (U1242 and U251) in presence of similar concentrations of TSA (25 nM) and/or CMP5 (25 uM). As a control, we utilized a flow cytometric assay to evaluate symmetric dimethyl H4R3 (S2Me-H4R3, FIG. 18) content and confocal microscopy (not shown) to verify decrease of methylation status. We used Aimexin V/PI staining and flow cytometry to examine apoptosis (below). In FIG. 18, use of single agent CMP5 (green) or TSA (blue) showed no change in S2Me-H4R3, however combination treatment (red) showed significant loss of methylation. We are presently performing dose response experiments to examine whether this activity can be improved. In data not shown, we can achieve similar results with lower doses of CMP5 (10 uM). Anti tumor, proapoptotic activity was enhanced in a synergistic fashion when low dose CMP5 was used in combination with the HDAC inhibitor TSA (FIG. 19). Inhibition PRMT5 with CMP5 and HDAC enzymes (at 10 fold lower concentrations) leads to synergistic induction of apoptosis of astrocytoma cell lines.

Synergistic Effect of the Combination of CMP5, Trichostatin A (HDAC Inhibitor) and 5-Azacytidine (DNA Methyltransferase Inhibitor) in Promoting Cell Death.

Figure 20:
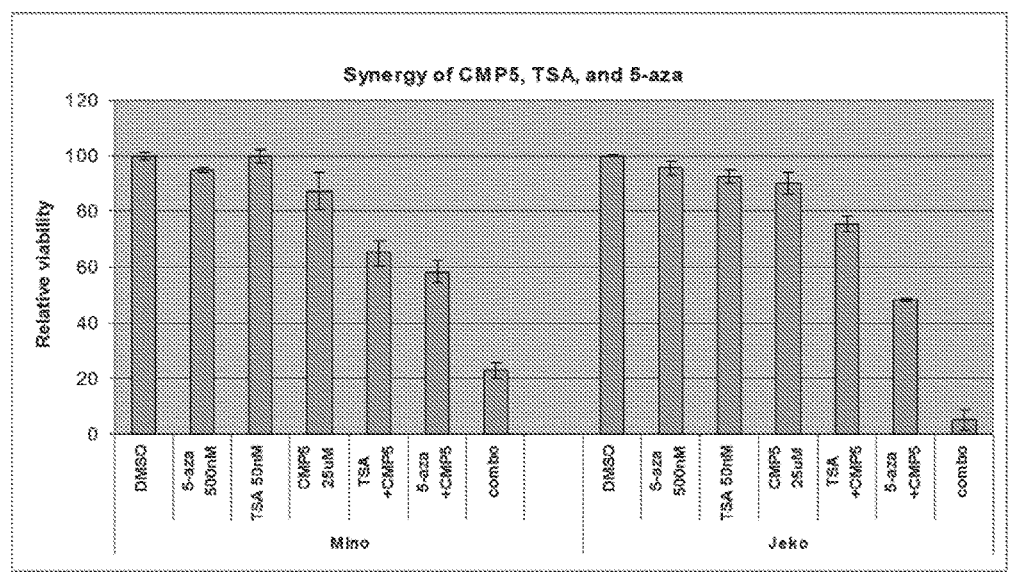
FIG. 20 shows (A) 5-aza, TSA, and CMP5 led to synergistic effects in inducing cell death. Jeko and Mino cells were treated with sub-toxic dose of 5-aza, TSA, CMP5 and combination of these drugs. Viability was evaluated by flow cytometry. (B, C) Jeko cells were treated by 25 uM of CMP5, 50 uM of TSA, and combo, expression of S2Me-H4R3 were detected by western blot (B) and confocal microscope (C).
Figure 20:
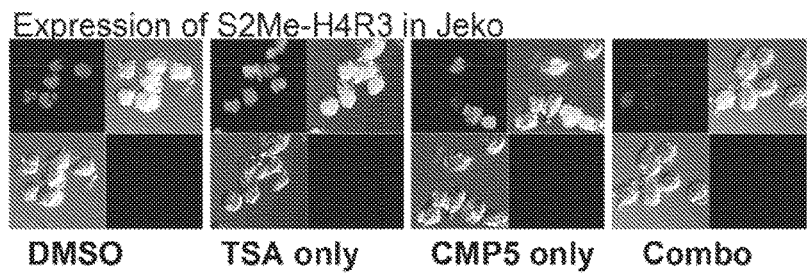
Figure 20:
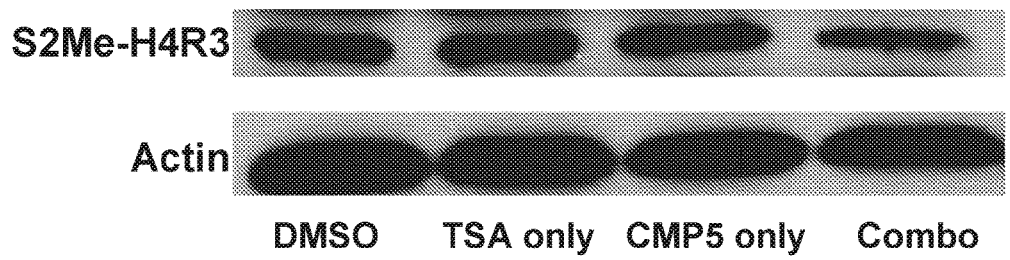

Because PRMT5 associates with other transcriptional co-repressors such as HDAC2 and DNMT3a, evaluation of synergistic effects between HDAC and DNA methylation inhibitors and PRMT5 inhibitors was performed in vitro. We have observed that sub toxic doses of DNA methyltransferase inhibitor 5-aza, HDAC inhibitor Trichostatin A (TSA), and PRMT5 inhibitor CMP5 led to synergistic induction of cell death (by flow cytometry, FIG. 20A) and loss of S2Me-H4R3 (by confocal microscopy and western blot) (FIGS. 20B and 20C).

Development of More Potent and Selective Analogs of CMP5.

Figure 21:
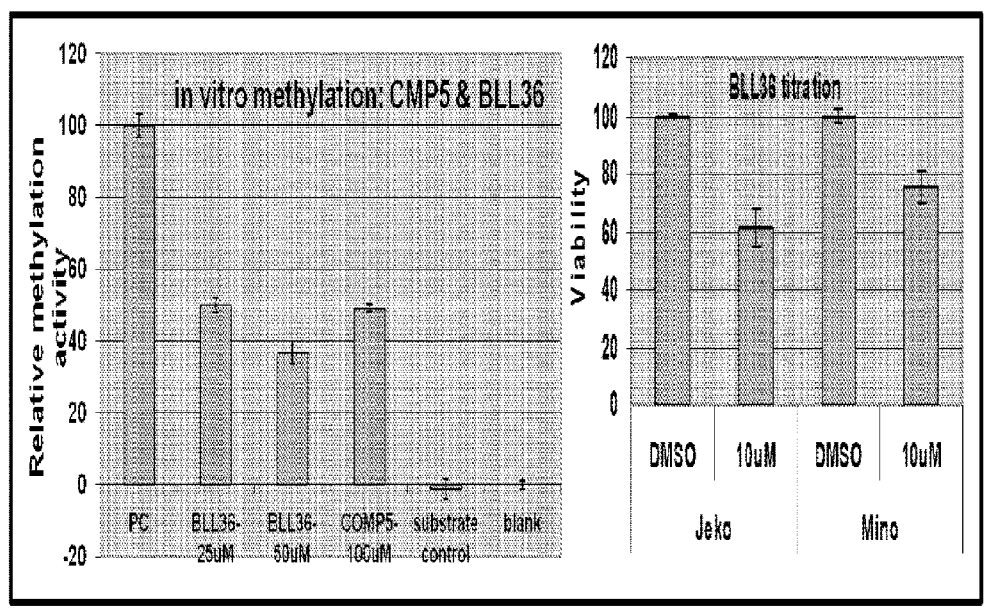
FIG. 21 shows (left) in vitro methylation assay showed BLL36 decreased methyltransferase activity of PRMT5 at a lower concentration than CMP5 (25 uM v.s. 100 uM). SAM was omitted for the substrate control, and human pure PRMT5 enzyme was omitted for blank control. (right) Jeko and Mino cells were treated by 10 uM of BLL36 for 24 hr, viability was evaluated by flow cytometry.
Figure 22:
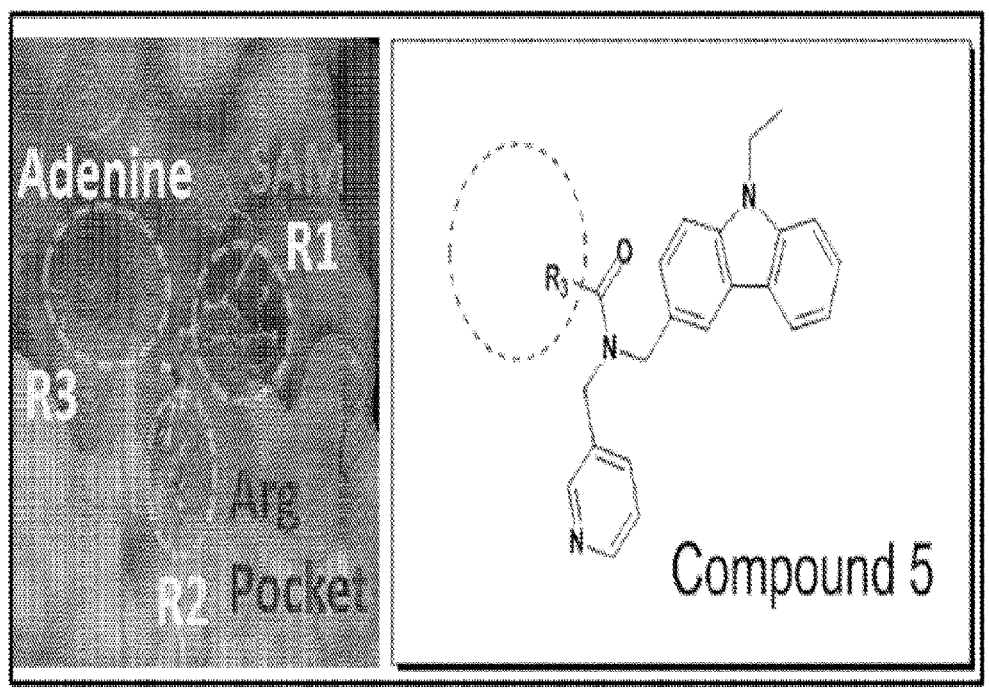
FIG. 22 shows optimization of CMP5. Left, R3 will be attached to CMP5 to mimic the interaction between cofactor adenine ring and PRMT5. Right, structure of CMP5 and the position where R3 will be attached.
Figure 23:
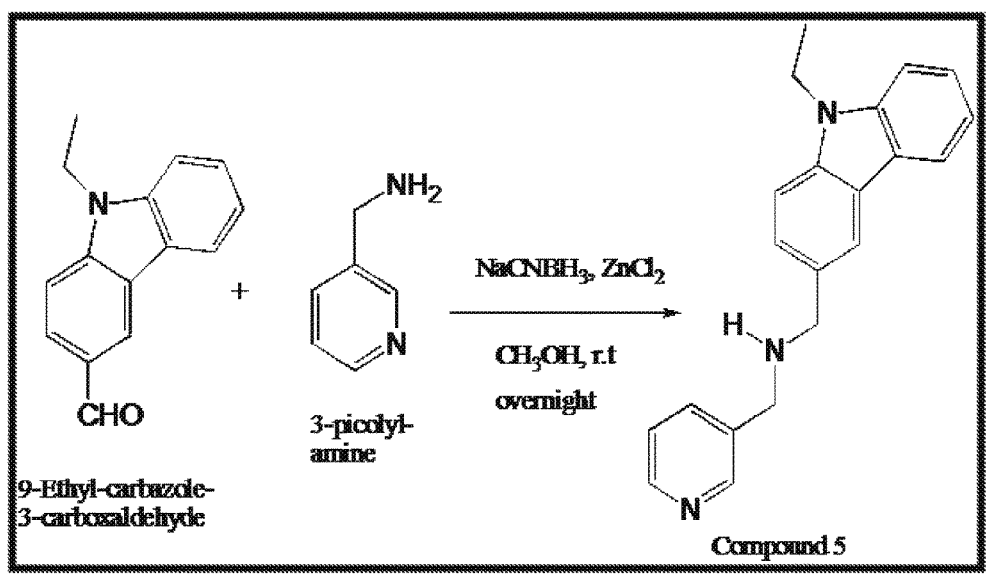
FIG. 23 shows a novel chemical synthesis for compound 5.

The lead compound identified in our initial screen showed an IC50 in micromolar (uM) ranges. Thus, a structure-based computational combinational lead optimization (FIG. 22) was used to design more potent analogs. Forty CMP5 analogs were designed and synthesized, one of the analogs (BLL36) was shown to be more selective and potent than CMP5 in terms of ability to inhibit methyltransferase activity (FIG. 21A) and to induce cell death (FIG. 21B).

The invention claimed is:
1. A compound of the formula:

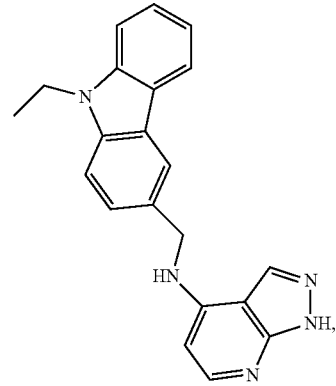

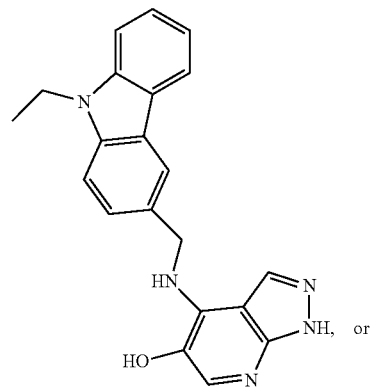

or

-continued

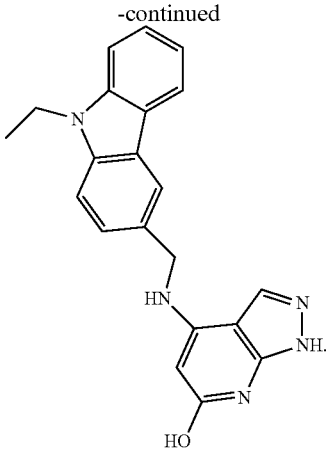

2. A pharmaceutical composition comprising a compound of claim 1 and a pharmaceutically suitable carrier.

3. The pharmaceutical composition of claim 2 further comprising at least one histone deacetylase (HDAC) inhibitor.

4. The pharmaceutical composition according to claim 2 further comprising at least one hypomethylating agent.

5. The compound according to claim 2, wherein the compound is:

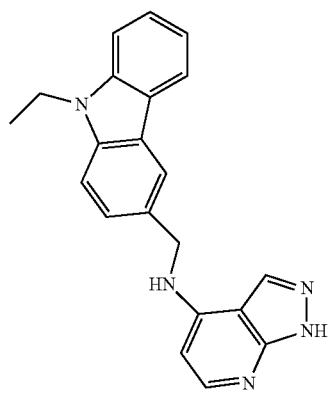 [SMILES: CCn1c2ccccc2c2cc(CNc3ccnc4[nH]ncc34)ccc21]

or a salt thereof.

6. The compound according to claim 1, wherein the compound is:

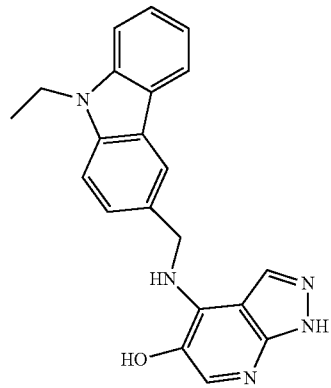 [SMILES: CCn1c2ccccc2c2cc(CNc3c(O)cnc4[nH]ncc34)ccc21]

or a salt thereof.

7. The compound according to claim 1, wherein the compound is:

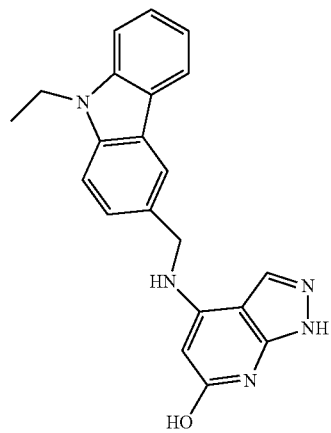 [SMILES: CCn1c2ccccc2c2cc(CNc3cc(O)nc4[nH]ncc34)ccc21]

or a salt thereof.

* * * * *